(12) United States Patent
Motomura et al.

(10) Patent No.: US 7,720,518 B2
(45) Date of Patent: May 18, 2010

(54) NUCLEAR MEDICAL DIAGNOSTIC EQUIPMENT AND DATA ACQUISITION METHOD FOR NUCLEAR MEDICAL DIAGNOSIS

(75) Inventors: Nobutoku Motomura, Tochigi-Ken (JP); Masuo Hayashi, Osaka (JP); Syouji Horiuchi, Izumiotsu (JP); Yoshifumi Nisawa, Toyonaka (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 371 days.

(21) Appl. No.: 11/020,280

(22) Filed: Dec. 27, 2004

(65) Prior Publication Data
US 2005/0187465 A1   Aug. 25, 2005

(30) Foreign Application Priority Data
Jan. 5, 2004   (JP) ............. P2004-000627

(51) Int. Cl.
*A61B 5/05* (2006.01)
(52) U.S. Cl. ............. 600/407; 600/427; 600/428
(58) Field of Classification Search .......... 600/428, 600/427, 443, 534, 407–409; 250/363.05
See application file for complete search history.

(56) References Cited

U.S. PATENT DOCUMENTS 4,645,933 A * 2/1987 Gambini et al. ........ 250/363.05
6,878,941 B2 * 4/2005 Balan et al. ............ 250/363.02
7,087,903 B2 * 8/2006 Balan et al. ............ 250/363.02
7,182,083 B2 * 2/2007 Yanof et al. ............ 128/204.23
7,194,062 B2 * 3/2007 Balan et al. .................... 378/15
2006/0074300 A1 * 4/2006 Green

FOREIGN PATENT DOCUMENTS

JP   2001-346773   12/2001

OTHER PUBLICATIONS

Bruyant et al. "Correction of the respiratory motion of the heart by tracking of the center of mass of thresholded projections: a simulation study using the dynamic MCAT phantom", IEEE Transactions on Nuclear Science, vol. 49, No. 5, Oct. 2002.*

* cited by examiner

*Primary Examiner*—Long V Le
*Assistant Examiner*—Sanjay Cattungal
(74) *Attorney, Agent, or Firm*—Oblon, Spivak, McClelland, Maier & Neustadt, L.L.P.

(57) ABSTRACT

A nuclear medical diagnostic equipment wherein radiation which is emitted by a nuclide administered into the body of a patient is detected as projection data by a gamma camera, and an image which indicates the distribution of the nuclide within the body of the patient is obtained on the basis of the projection data. The equipment comprises a rotation unit which rotates the radiation detector round the patient, a respiration identification unit which identifies breathing of the patient and non-breathing thereof based on breath holding, a data storage unit in which the radiation detection data acquired by the radiation detector are stored in an identifiable manner on the basis of a result of the identification by the respiration identification unit, and an image generation unit which generates the image from the radiation detection data stored in the data storage unit on the basis of the result of the identification by the respiration identification unit.

19 Claims, 15 Drawing Sheets

NUCLEAR MEDICAL DIAGNOSTIC EQUIPMENT AND DATA ACQUISITION METHOD FOR NUCLEAR MEDICAL DIAGNOSIS

BACKGROUND OF THE INVENTION

1. Field of the Invention

The present invention relates to a nuclear medical diagnostic equipment and a data acquisition method for a nuclear medical diagnosis wherein radiation emitted from a nuclide (radioisotope: RI) administered to a patient is detected using a gamma (γ) camera, and an RI distribution is imaged on the basis of the detection information.

2. Description of the Related Art

With the technological advancements of hardware and software in recent years, a nuclear medical diagnostic equipment being an equipment for medical use has also made great progress.

The nuclear medical diagnostic equipment includes a measurement unit called "gamma camera", and it is employed for implementing the nuclear medical examination of a patient. The nuclear medical examination is implemented in such a way that, as stated above, a drug labeled with a radioisotope (hereinbelow, abbreviated to "RI") is administered into the body of a patient, whereupon an RI distribution within the body is imaged by a gamma camera. The principal techniques of the nuclear medical examination are a planar method (taking the static image of the patient in a fixed direction), and a SPECT method (single photon emission computed tomography: SPECT; taking the tomogram of the patient).

In the case of the nuclear medical examination, a time period of several minutes to several tens minutes is usually expended in acquiring data. Therefore, the data cannot be acquired in the state of one time of breath holding by the patient, over the whole data acquisition time period. That is, the data must be acquired even while the patient is breathing. Accordingly, an acquired image is influenced by bodily motions ascribable to the respiration of the patient. Thus, the image quality of the acquired image, including a positional resolution and a contrast, degrades inevitably.

A technique which acquires data in synchronism with data acquiring phases (respiratory phases) set on a spirogram detected from a patient, in order to reduce or avoid the influence of the bodily motions ascribable to the respiration, has been known as seen from, for example, Kazunori Kan, et al.: "Initial experience of Respiratory-gated lung ventilation/blood flow SPECT examination", page 590 of proceeding "Nuclear Medicine", November 2002 (Volume 39, No. 4) issued on Nov. 20, 2002 by the Japanese Society of Nuclear Medicine, and Kazunori Kan, et al.: "Lung ventilation/blood flow SPECT based on Automatic superposition software", page 590 of proceeding "Nuclear Medicine", November 2002 (Volume 39, No. 4) issued on Nov. 20, 2002 by the Japanese Society of Nuclear Medicine. In the case of the data acquisition method, when the respiratory phases to be used for the data acquisition are divided more finely, the influence of the bodily motions ascribable to the respiration can be reduced to a considerable degree.

Further, JP-A-2001-346773 discloses a technique in which the respiratory movement of a patient is detected by a respiration detection device, and an imaging device is controlled so as to acquire data in respiratory rest periods of small bodily motions in accordance with the detected respiratory movement.

In the case of the above respiratory-gated data acquisition, however, acquisition counts per finer phase decrease basically, and hence, statistic noise and the like noise become predominant, to pose the problem that the degradation of an image is incurred due to the noise. In a case where the respiratory phases are coarsely divided contrariwise, there is incurred a contradictory situation where the image degradation ascribable to the decrease of the acquisition counts can be relieved, but where the effect of suppressing the influence of the bodily motions ascribable to the respiration decreases.

Further, the respiratory-gated data acquisition is performed using a respiratory gating monitor. In this regard, it is pointed out that the respiratory gating monitor sometimes fails to reliably sense the breathing state of the patient. In such a case where the breathing state cannot be reliably sensed, the extension of the data acquisition time period or the decrease of the acquisition counts is incurred, resulting in a situation where the throughput of the patient lowers or where the image degradation becomes drastic.

Still further, in the case of the respiratory-gated data acquisition, the image is taken under the averaged bodily motion of the patient over the total time of the individual data acquiring respiratory phases. Therefore, the respiratory-gated data acquisition is not a little influenced by the bodily motions ascribable to the respiration, as compared with data acquisition in the non-breathing state of the patient, so that the image quality of the acquired image is unsatisfactory.

Meanwhile, as another problem it is permitted to acquire the data only in the respiratory rest periods of the patient. When an image is generated using only the data acquired in the respiratory rest periods, the degradations of the positional resolution and contrast of the image attributed to the bodily motions of the patient can be suppressed. In this case, however, data are not acquired in the respiratory periods or breathing state of the patient. This poses the problem that the number of samplings decreases to degrade the smoothness, namely, sensitivity of the image.

It is therefore desired to develop a technique for taking an image of higher positional resolution and sensitivity in compliance with clinical purposes.

SUMMARY OF THE INVENTION

The present invention alleviates the problems involved in the related art concerning the bodily motions of a patient and the image quality of an acquired image, and it has for its object to provide in the data acquisition of nuclear medicine wherein data cannot possibly be acquired in one time of breath holding period, a nuclear medical diagnostic equipment and a data acquisition method for a nuclear medical diagnosis as can obtain a diagnostic image of high image quality by excluding influence that bodily motions attendant upon the respiration of a patient exert on the degradation of the image quality, with breath holding conducted in a state where the patient is hardly burdened.

Besides, the invention has been made in order to cope with the circumstances of the related art as stated before, and it has for its object to provide in the data acquisition of nuclear medicine wherein data cannot possibly be acquired in one time of breath holding period, a nuclear medical diagnostic equipment and a data acquisition method for a nuclear medical diagnosis as can take an image at a higher positional resolution and a higher sensitivity in compliance with clinical purposes, with breath holding conducted in a state where a patient is hardly burdened.

In order to accomplish the above objects, according to one aspect of the invention, there is provided a nuclear medical diagnostic equipment wherein radiation which is emitted by a nuclide administered into a body of a patient is detected as projection data by a radiation detector, and an image which indicates a distribution of the nuclide within the body of the patient is obtained on the basis of the projection data. The nuclear medical diagnostic equipment is characterized by comprising a rotation unit which rotates the radiation detector round the patient; a respiration identification unit which identifies breathing of the patient and non-breathing thereof based on breath holding; a data storage unit in which the radiation detection data acquired by the radiation detector are stored in an identifiable manner on the basis of a result of the identification by the respiration identification unit; and an image generation unit which generates the image from the radiation detection data stored in the data storage unit on the basis of the result of the identification by the respiration identification unit.

Besides, according to another aspect of the invention, there is provided a nuclear medical diagnostic equipment wherein radiation which is emitted by a nuclide administered into a body of a patient is detected as projection data by a radiation detector, and an image which indicates a distribution of the nuclide within the body of the patient is obtained on the basis of the projection data. The nuclear medical diagnostic equipment is characterized by comprising a rotation unit which rotates the radiation detector round the patient; and an image generation unit which generates the image by using the radiation detection data acquired by the radiation detector in a breathing state of the patient and a non-breathing state thereof based on breath holding, respectively.

Further, according to another aspect of the invention, there is provided a data acquisition method for a nuclear medical diagnosis wherein radiation which is emitted by a nuclide administered into a body of a patient is detected as projection data by a radiation detector. The data acquisition method is characterized by comprising obtaining identification information which identifies a breathing state of the patient and a non-breathing state thereof based on breath holding; and storing the projection data in a manner to be capable of identifying whether the projection data have been acquired in the non-breathing state or in the breathing state, by the identification information.

Still further, according to another aspect of the invention, there is provided a data acquisition method for a nuclear medical diagnosis wherein radiation which is emitted by a nuclide administered into a body of a patient is detected as projection data by a radiation detector. The data acquisition method is characterized by comprising storing the projection data which have been acquired by the radiation detector in a breathing state of the patient and a non-breathing state thereof based on breath holding, respectively, in a manner to be capable of identifying whether the projection data have been acquired in the non-breathing state or in the breathing state; and generating an image by using both the projection data acquired in the non-breathing state and the projection data acquired in the breathing state.

In accordance with the nuclear medical diagnostic equipments and the data acquisition methods therefor according to the invention as described above, in the data acquisition of nuclear medicine wherein data cannot possibly be acquired in one time of breath holding period, a diagnostic image of high image quality can be obtained by excluding influence which bodily motions attendant upon the respiration of the patient exert on the degradation of the image quality, with the breath holding conducted in a state where the patient is hardly burdened.

Besides, in the data acquisition of nuclear medicine wherein data cannot possibly be acquired in one time of breath holding period, an image can be taken at a higher positional resolution and a higher sensitivity in compliance with clinical purposes, with the breath holding conducted in a state where the patient is hardly burdened.

DETAILED DESCRIPTION OF THE PREFERRED EMBODIMENTS

Now embodiments of a nuclear medical diagnostic equipment and a data acquisition method for a nuclear medical diagnosis according to the present invention will be described with reference to the drawings.

1. First Embodiment

A nuclear medical diagnostic equipment and a data acquisition method for a nuclear medical diagnosis according to the first embodiment of the invention will be described with reference to FIG. 1-FIG. 4.

Figure 1:
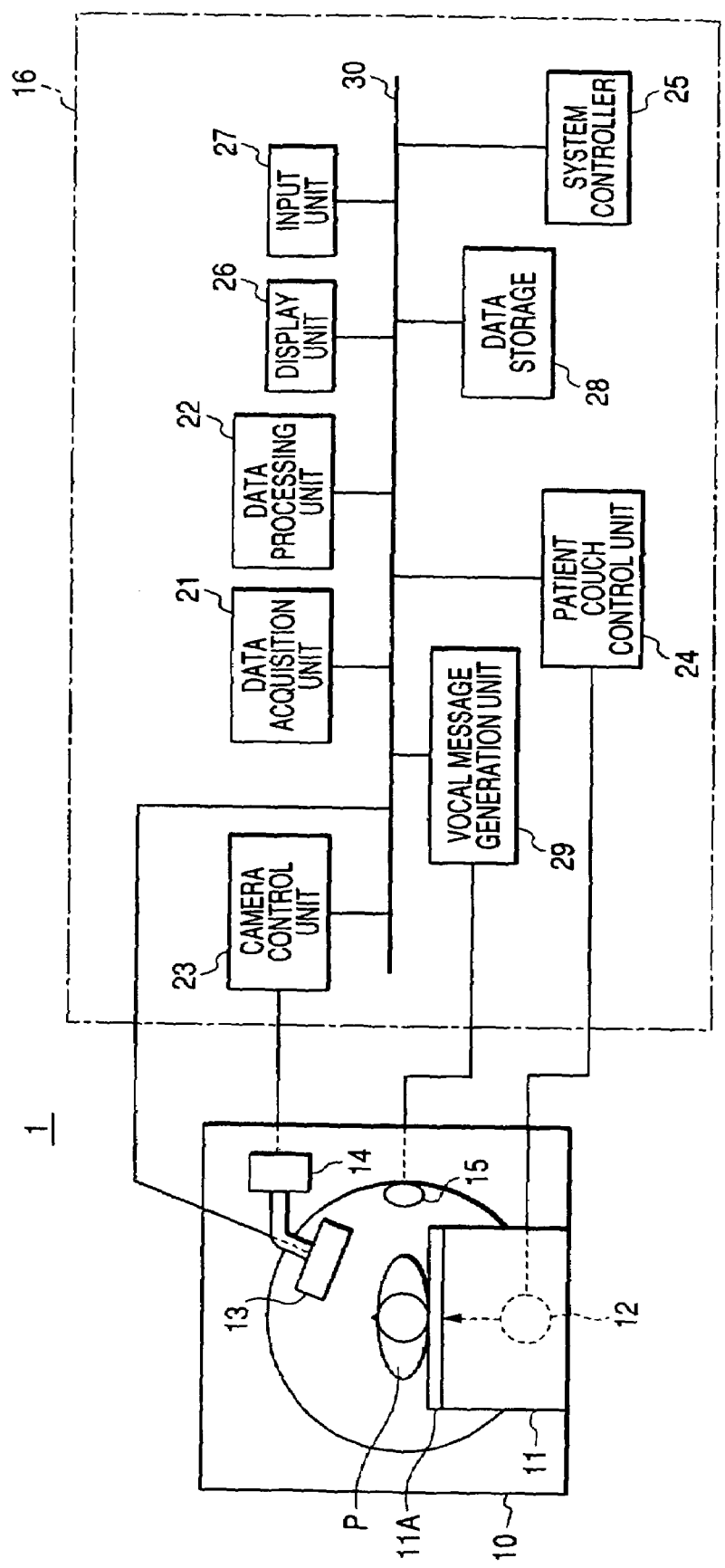
FIG. 1 is a functional block diagram showing the outline of a nuclear medical diagnostic equipment according to the first embodiment of the invention.

FIG. 1 shows the schematic construction of a nuclear medical diagnostic equipment 1 according to this embodiment. The nuclear medical diagnostic equipment 1 includes a patient couch 11 with a tabletop 11A on which a patient P lies down, usually with the face upward, a patient couch driver 12 which is built in the patient couch 11, a gantry 10 which is arranged in adjacency to the patient couch 11, a gamma camera 13 which is held by the gantry 10, a camera driver 14 which is disposed in the gantry 10 and which drives the gamma camera 13 so as to be movable, a loudspeaker 15, and a control/processing device 16.

The control/processing device 16 includes a data acquisition unit 21, a data processing unit 22, a camera control unit 23, a patient couch control unit 24, a system controller 25, a display unit 26, an input unit 27 which an operator manipulates, a data storage 28 which is a data storage unit for storing image data therein, and a vocal message generation unit 29. These units 21-29 are connected through an internal bus 30 so as to be communicable with one another.

The gamma camera 13 detects radiation emitted from a nuclide (radioisotope: RI) injected into the body of the patient P, as the distribution of gamma (γ) rays in two dimensions, and it sends the detected result to the data acquisition unit 21. The gamma camera 13 has a two-dimensional detection portion employing, for example, a scintillator, and it detects the γ rays entering a detection face. This gamma camera 13 may well have the detection portion in which semiconductor cells are arranged in the shape of a two-dimensional array.

The data acquisition unit 21 subjects the detection signal sent from the gamma camera 13, to appropriate processing, thereby to generate the projection data of the two-dimensional pixel region (detection face) in a digital quantity, and it sends the projection data to the data processing unit 22.

In case of a planar method, the data processing unit 22 generates a projection image as viewed in a certain fixed radiographing direction (position). On the other hand, in a case where a SPECT method is performed, the data processing unit 22 subjects the projection data detected in individual radiographing directions (positions), to pre-processing (such as the correction of the rotational center of the gamma camera, and the correction of uniformity), and besides, to a series of processing called "a filter-correction inverse projection method", based on the generation of a sinogram, and convolution, back projection and attenuation corrections. Thus, it reconstructs a SPECT image being a tomogram, out of the projection data in the multiple radiographing directions.

The camera control unit 23 feeds the camera driver 14 with a control signal in order to control the spatial movement of the gamma camera 13, under the control of the system controller 25. Thus, the gamma camera 13 can freely alter its radiographing direction and position in accordance with the drive by the camera driver 14. That is, the camera driver 14 functions as a rotation unit which rotates the gamma camera 13 being the radiation detector round the patient P.

Besides, the patient couch control unit 24 operates under the control of the system controller 25 and can control the position of the tabletop 11A through the patient couch driver 12. The display unit 26 can display the projection image or the SPECT image generated by the data processing unit 22, and it can also display manipulation information given through the input unit 27 by the operator. The input unit 27 is used in order that the operator may give the necessary manipulation information. Therefore, the display unit 26, the input unit 27, and the system controller 25 to be explained later constitute a user interface.

The vocal message generation unit 29 generates vocal message data, such as "Please hold your breath at the sign of the next peep" or "Please breathe", automatically in compliance with an instruction from the system controller 25, and it sends the generated data to the loudspeaker 15 attached to the gantry 10. Since the loudspeaker 15 consequently outputs such a vocal message, the patient P lying near the loudspeaker 15 hears the vocal message and conducts, for example, breath holding in a data acquisition mode to be explained later.

The system controller 25 controls the whole equipment in accordance with command information from the operator and drive information for the various portions of the equipment, so as to generate the image (projection image, SPECT image) for the nuclear medical diagnosis on the basis of the detection signal of the gamma camera 13. Also, it executes a control for data acquisition as features the invention.

The data acquisition is a technique which takes into consideration the length of a data acquisition time period that is several minutes in the planar method and several tens minutes in the SPECT method. More specifically, it is impossible that the patient P conducts breath holding which continues for such a long acquisition time period. Therefore, the patient P is caused to intermittently conduct temporary breath holdings (breath stops) of reasonable time periods, and the data acquisition for the nuclear medical diagnosis, in other words, the detection of the gamma rays is done only in the state of the temporary breath stop (in the non-breathing state). The inventors have called the data acquisition method the "intermittent data acquisition method". According to the "intermittent data acquisition method", data are acquired in the non-breathing (temporary breath stop) state for a period of certain predetermined length, and data are acquired while the patient P is taking breath (in the breathing state), for the next period of predetermined length or desired length. Only the data acquired in the individual time zones of the non-breathing state, among the data thus acquired, are extracted so as to generate the image (that is, the data acquired in the individual time zones of the breathing state are not adopted for the image generation).

Figure 2:
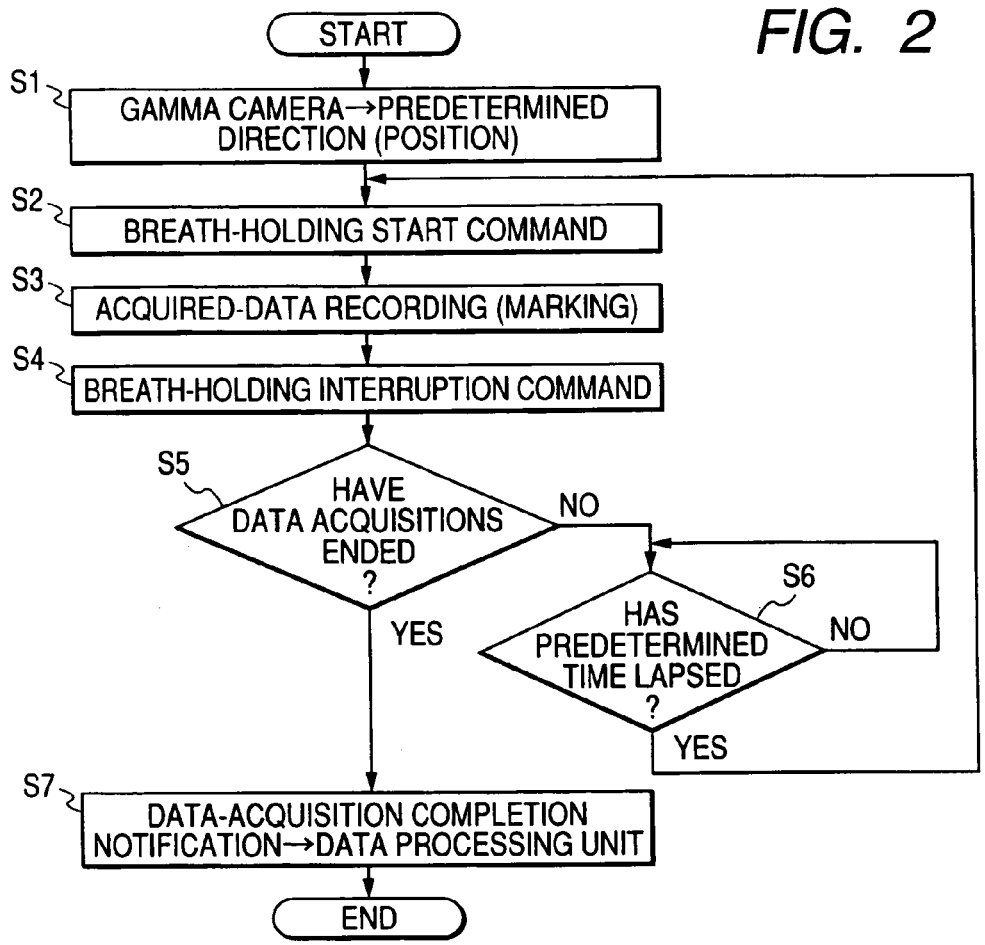
FIG. 2 is a flow chart showing the outline of the data acquisition control of a planar method applying an "intermittent data acquisition method" as is performed in the first embodiment.

FIG. 2 shows the outline of a process in the case where the "intermittent data acquisition method" is applied to the planar method as the data acquisition method of this embodiment. Incidentally, the process of the "intermittent data acquisition method" applied to the planar method as shown in FIG. 2 is executed by the system controller 25 in this embodiment, but it may well be executed by a control unit dedicated to the data acquisition control.

The operation of the "intermittent data acquisition method" applied to the planar method will be described with reference to FIGS. 2 and 3.

In a case where the equipment 1 has been commanded to perform the planar method by the operator, the system controller 25 successively executes processing steps shown in FIG. 2. The gamma camera driver 14 is driven through the camera control unit 23 so that the radiographing direction of the gamma camera 13 (and the position thereof from the surface of the body) for the desired diagnostic part of the patient P may be set at a commanded predetermined radiographing direction (position) (step S1). On this occasion, if necessary, the tabletop driver 12 is driven through the patient couch control unit 24 so as to set the position of the tabletop 11A (such as the position of this tabletop in the longitudinal direction thereof).

Subsequently, the system controller 25 drives the vocal message generation unit 29 so as to automatically issue the message, for example, "Please hold your breath at the sign of the next peep" from the loudspeaker 15 (step S2). Thus, the patient P temporarily stops his/her breath in compliance with the sign "peep" heard subsequently to the issued breath-holding command. Incidentally, the breath holding should preferably be practiced before the actual diagnosis so that the patient P may be capable of conducting it at the sign.

In this manner, the system controller 25, vocal message generation unit 29 and loudspeaker 15 constitute a command unit which gives the command of the breath holding period of the patient P, while the system controller 25 and data acquisition unit 21 constitute an acquisition unit which acquires the projection data detected by the gamma camera 13 being the radiation detector, in synchronism with the breath holding period commanded by the command unit. Further, the command unit and acquisition unit constitute a respiration identification unit which identifies the non-breathing state and breathing state of the patient P. Herein, the message of the breath holding command is automatically issued by the respiration identification unit, whereby the non-breathing state and the breathing state can be identified.

The system controller 25 subsequently sends a command to the data acquisition unit 21 so as to mark acquired data which are recorded after the start of the breath holding (step S3). The data acquisition unit 21 is always processing the detection signal sent from the gamma camera 13, into the projection data. When the breath-holding start command has been given, the data acquisition unit 21 synchronously marks the projection data to be processed after the command, with a flag or the like, and it subsequently stores the projection data in the data recording unit 28. Thus, in the data recording unit 28, the projection image data acquired and processed in the non-breathing state are distinguished from the projection image data acquired and processed without the breath holding (in the breathing state).

That is, the data acquisition unit 21 affixes identification information for the identification between the non-breathing state and the breathing state, to the projection data by, for example, the marking, and it writes the identification information into the data recording unit 28.

Incidentally, the data acquisition based on the marking should desirably be performed with a delay of predetermined time period (for example, about one second) since the sign of the breath holding so as to be done in a state where the patient P has held his/her breath without fail.

Subsequently, upon completion of the recording of the acquired data based on the marking, for a time period (for example, about 10 seconds) during which the patient P can continue his/her breath holding substantially reasonably, the system controller 25 drives the vocal message generation unit 29 to automatically issue the message, for example, "Please breathe" from the loudspeaker 15 (step S4). Thus, the patient P temporarily interrupts the breath holding in compliance with the message.

Thereafter, the system controller 25 judges whether or not the data acquisitions based on the planar method have been completed (step S5). The judgment is made on the basis of an index, for example, whether or not the total time period of the temporary breath stops based on the breath holdings has reached a predetermined time period, or whether or not the number of times of the breath holdings has reached a predetermined value. In a case where the data acquisitions have been completed ("YES" at the step S5), the data acquisition mode is ended. However, in a case where the data acquisitions have not been completed yet ("NO" at the step S5), the lapse of a predetermined time period td (for example, about 10-15 seconds) is waited (step S6), whereupon the above processing steps S2-S5 are iterated a plurality of times again. Accordingly, the patient P is allowed to freely breathe during such a predetermined time period td.

In a case where the completion of the data acquisitions has been judged in the course of the iteration ("YES" at the step S5), the system controller 25 outputs a notification of the completion, to the data processing unit 22 (step S7). In response to the notification, the data processing unit 22 reads out the marked projection image data stored in the data storage 28 and executes the pixel additions of the read-out data, thereby to generate the data of the final projection image. The data of the projection image are displayed on the display unit 26, and are stored in the data storage 28.

That is, the data processing unit 22 functions as an image generation unit, which chooses the projection image data for use in the data generation for the final projection image, on the basis of the identification information of the projection image data as affixed by the marking, and which thereafter generates the data of the final projection image from only the projection image data obtained in the non-breathing state.

Figure 3:
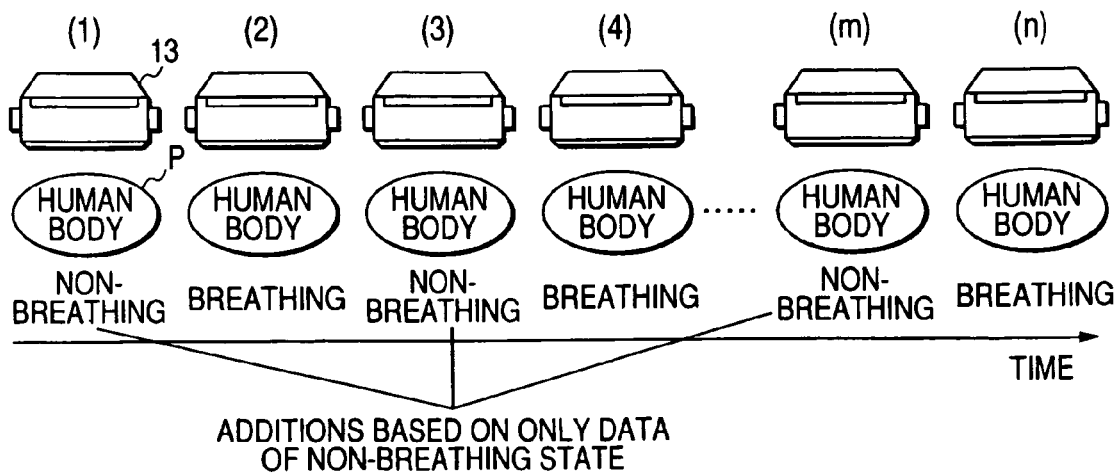
FIG. 3 is a diagram for explaining the concept of non-breathing and breathing in the data acquisition control of the planar method as shown in FIG. 2.

Thus, according to this embodiment, as shown in model-like fashion in FIG. 3, the planar method whose radiographing time period is usually as long as several minutes proceeds in such a way that the breath holdings each being for a short time period (about 10 seconds) for which the breath can be temporarily stopped are iterated a plurality of times (refer to (1), (3), and (m) in FIG. 3), and that the necessary data are acquired in the total time period of the breath holdings. The final projection image is obtained by adding the data of the projection images acquired in the respective breath stop periods, every pixel.

In this manner, the patient P can adjust his/her respiratory state in the free breathing period between the breath holding periods, and he/she can reasonably conduct the temporary breath stop based on the next breath holding. The breath-holding acquisitions are, of course, reasonable in themselves. Moreover, since the bodily motions of the patient P lessen owing to the reasonable breath holdings, the positional resolution and contrast of the projection image finally obtained are high. Furthermore, since the acquisition counts of the data acquisitions are ensured, noise is low. It is accordingly possible to obtain the projection image, namely, the static image of the patient P in the fixed direction, which has a remarkably higher image quality than in the related art. The radiographing based on the planar method requires several minutes ordinarily, and this embodiment requires a longer radiographing time period. However, the merit of the obtainment of the projection image of high image quality more than negates the drawback of the extended radiographing time period. Moreover, the possibility of re-radiographing lowers sharply, so that the patient P is less burdened ultimately to become easier of being diagnosed.

Incidentally, the patient P need not always be given the instructions of the timings of the start and interruption of the breath holding by the above construction based on the automatic voice generation (or automatic voice), but the operator may well give vocal instructions through a microphone or the like while watching the state of the patient P. Alternatively, character displays may well be presented by a panel, or light may well be turned ON and OFF for the instructions. That is, the respiration identification unit can be constituted by any desired constituent such as the microphone or the panel which is disposed in addition to, or in place of, the loudspeaker.

2. Modification to First Embodiment

Figure 4:
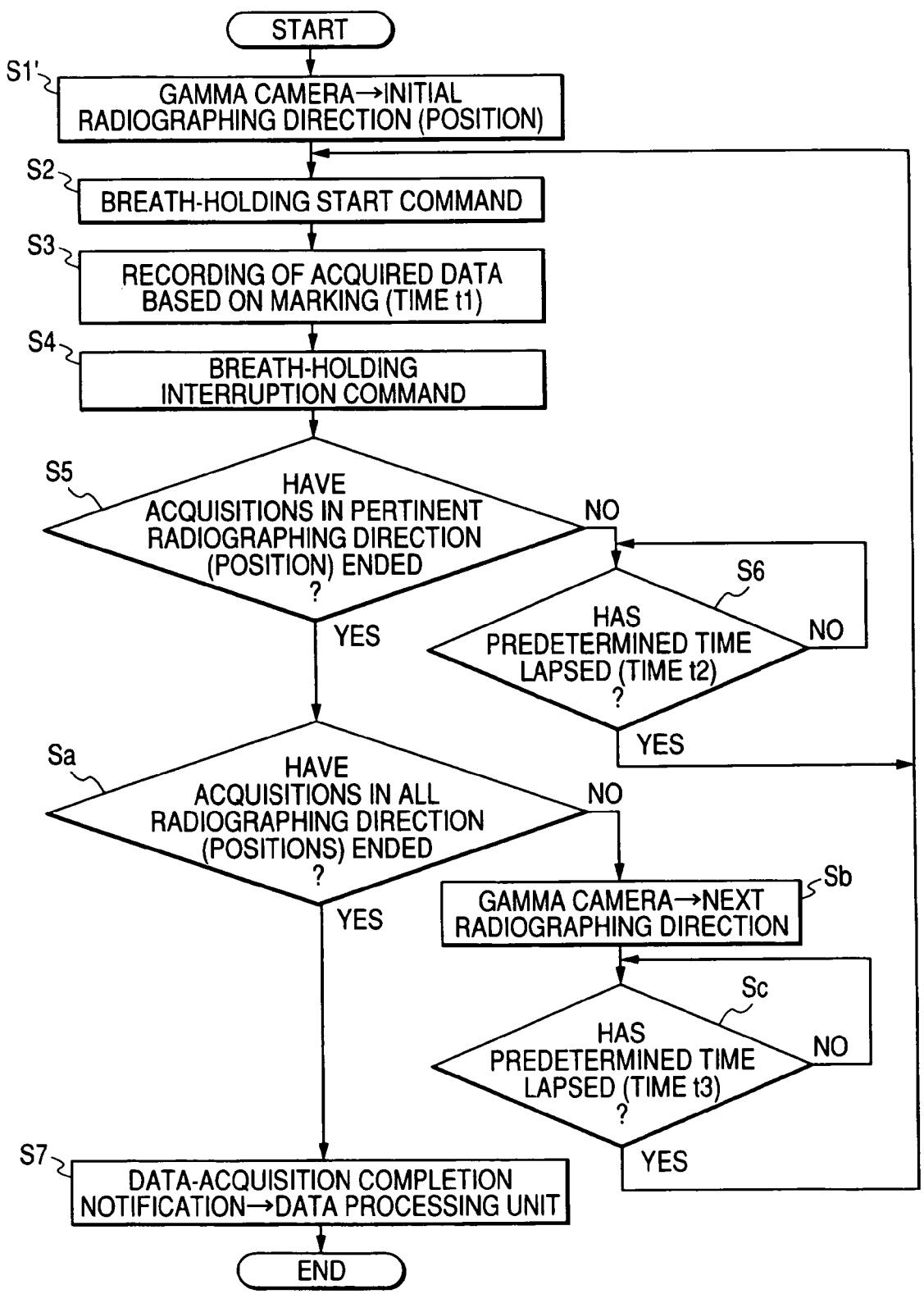
FIG. 4 is a flow chart showing the outline of the data acquisition control of a SPECT method applying the "intermittent data acquisition method" as is performed in a modification to the first embodiment.

FIG. 4 shows a modification to the first embodiment. A flow chart in FIG. 4 shows the process of the "intermittent data acquisition method" applied to the SPECT method as has expanded the process shown in FIG. 2. In FIG. 4, steps which execute processing identical or equivalent to the processing of the foregoing steps in FIG. 2 are denoted by the same signs.

In the "intermittent data acquisition method" applied to the SPECT method, the gamma camera 13 is first located in an initial radiographing direction (position) by the system controller 25 (step S1'), a command for the start of breath holding is given (step S2), and acquired data are recorded with identification information based on marking, for a time period t1 (step S3). Subsequently, a command for the interruption of the breath holding is given (step S4). Further, whether or not data acquisitions in the current radiographing direction (position) have been completed is judged (step S5). In a case where the data acquisitions have not been completed yet, a free respiration for a predetermined time period t2 is allowed, whereupon a temporary breath stop based on breath holding, and data acquisition are performed again (step S6, and steps S2-S5).

When the data acquisitions in one radiographing direction (position) have been completed by iterating the above steps, the system controller 25 judges whether or not data acquisitions in all preset radiographing directions (positions) have been completed (step Sa). In a case where the judgment is "NO", that is, where any radiographing direction (position) in which data are to be acquired is still existent, the system controller 25 instructs the camera control unit 23 to rotate the gamma camera 13 into the next radiographing direction (position) Thereafter, the lapse of a predetermined time period t3 is waited, whereupon the routine is returned to the step S2. Thus, a plurality of times of divided data acquisitions in the temporary non-breathing state as explained before are performed in the new radiographing direction (position).

When the data acquisitions in all the radiographing directions (positions) have ended in this way ("YES" at the step Sa), a data-acquisition completion notification is sent to the data processing unit 22. Then, the data processing unit 22 reads out the image data recorded with the identification information affixed thereto, from the data recording unit 28, and it executes the additions of the projection image data in the plurality of times of breath stop periods in the respective radiographing directions (positions), and the reconstruction of a SPECT image employing the projection image data in the plurality of radiographing directions (positions). Thus, the "intermittent data acquisition method" can be applied to the SPECT method, and that SPECT image of high image quality from which the image quality degradation ascribable to the bodily motions of the patient P has been excluded without fail can be obtained as described before.

Incidentally, the planar method and the SPECT method applying the "intermittent data acquisition method" as described above can be similarly carried out in a nuclear medical diagnostic equipment which performs tomography called "positron ECT (positron emission computed tomography: PET)", and a data acquisition method for the equipment.

3. Second Embodiment

Figure 5:
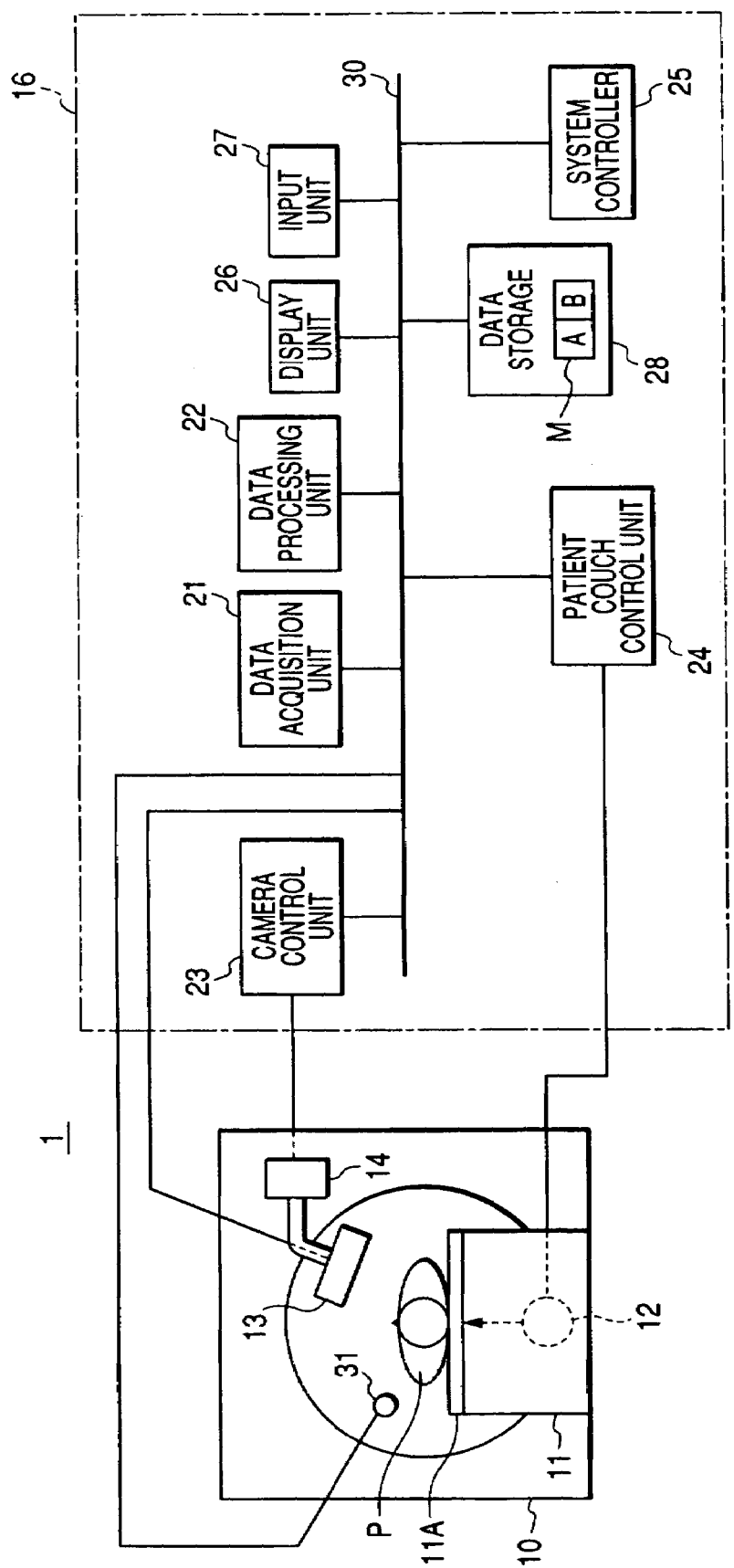
FIG. 5 is a functional block diagram showing the outline of a nuclear medical diagnostic equipment according to the second embodiment of the invention.

Next, the second embodiment of the invention will be described with reference to FIGS. 5-7.

A nuclear medical diagnostic equipment according to the second embodiment adopts such a construction that acquired data having responded to signals issued by a manipulation switch or the like, which is an example of a signal generation unit, are recorded separately in individual areas.

More specifically, a respiration identification unit which identifies a non-breathing state and a breathing state is constituted by the manipulation switch and also a system controller 25, a data acquisition unit 21 and a data recording unit 28. Besides, that area of the data recording unit 28 in which the acquired data have been recorded serves as identification information for identifying the non-breathing state and the breathing state.

Incidentally, the remaining construction and operation are the same as in the nuclear medical diagnostic equipment according to the first embodiment and shall therefore be omitted from description.

The manipulation switch of the nuclear medical diagnostic equipment according to the second embodiment is, for example, an ON/OFF switch. In the case of this embodiment, the manipulation switch is arranged at the hand of a patient P as indicated at reference sign 31 in FIG. 5. Therefore, the patient P can push the manipulation switch 31 by his/her own manipulation when starting and interrupting breath holding. Incidentally, an operator may well manipulate the manipulation switch 31 while instructing the patient P to hold his/her breath.

Besides, the data storage 28 has a memory M for storing therein the projection data acquired by the data acquisition unit 21, and the memory M is divided into memory areas A and B. The other hardware architecture of the nuclear medical diagnostic equipment is the same as the foregoing one in FIG. 1, except that the system controller 25 executes a process outlined in FIG. 6.

Figure 6:
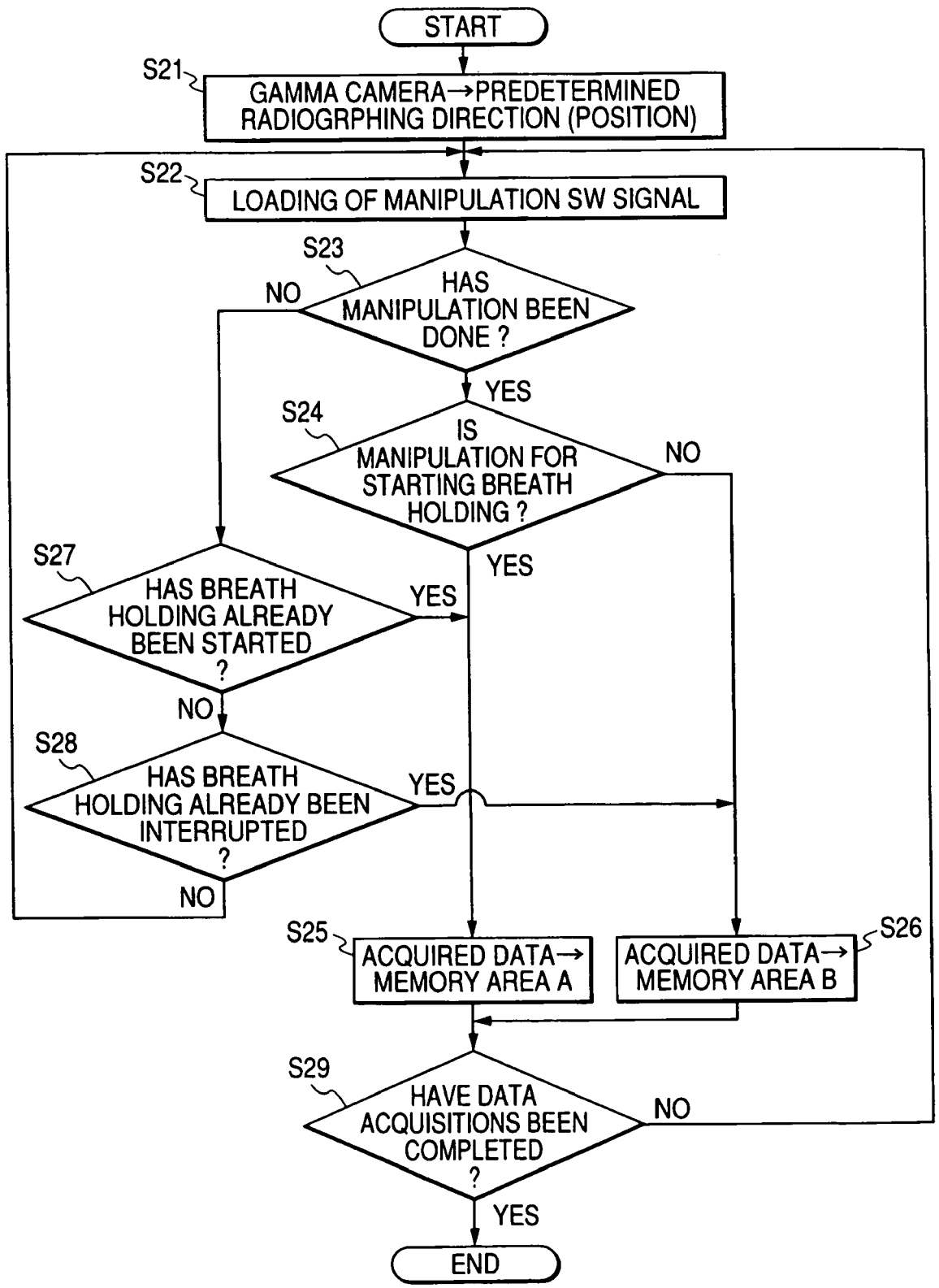
FIG. 6 is a flow chart showing the outline of the data acquisition control of a planar method applying an "intermittent data acquisition method" as is performed in the second embodiment.

FIG. 6 shows the process of a planar method to which the "intermittent data acquisition method" according to the invention is applied.

In accordance with the process, the system controller 25 locates a gamma camera 13 in a predetermined radiographing direction (and a predetermined position from the surface of the body of the patient P) (step S21), and it loads a switch signal from the manipulation switch 31 (step S22). Then, the system controller 25 judges whether or not the switch signal has been outputted, that is, whether or not the manipulation switch 31 has been manipulated (step S23). In a case where the manipulation switch 31 has been manipulated, the system controller 25 judges whether or not the manipulation of breath-holding start has been done in order that the patient P may start his/her breath holding by himself/herself (step S24).

In a case where the judgment indicates the manipulation of the breath-holding start ("YES" at the step S24), the system controller 25 controls the data acquisition unit 21 and the data recording unit 28 so that projection data acquired after the start of the breath holding may be recorded in the memory area A of the memory M of the data recording unit 28 (step S25). To the contrary, in a case where the judgment at the step S24 becomes "NO", the manipulation by the patient P indicates the interruption of breath holding, and hence, the system controller 25 controls the data acquisition unit 21 and the data recording unit 28 so that projection data acquired after the interruption of the breath holding may be recorded in the memory area B of the memory M of the data recording unit 28 (step S26).

Meanwhile, in a case where the judgment at the step S23 is "NO" signifying that the manipulation switch 31 has not been manipulated, whether or not the breath holding has already been started is further judged by, for example, flag processing (step S27) In a case where the judgment becomes "YES", the recording of the acquired data at the above step S25 is done. In contrast, in a case where the judgment of "NO" is rendered at the step S27, it is further judged whether or not the breath holding has already been interrupted (step S28). In a case where the judgment becomes "YES", the recording of the acquired data at the above step S26 is done. In a case where the judgment of "NO" is rendered at the step S28, any switch manipulation has not been done yet, and hence, the routine is returned to the step S22.

The above processing of the data recording is iteratively executed until data acquisitions of predetermined quantity in such a radiographing direction (position) have been completed (step S29).

Figure 7:
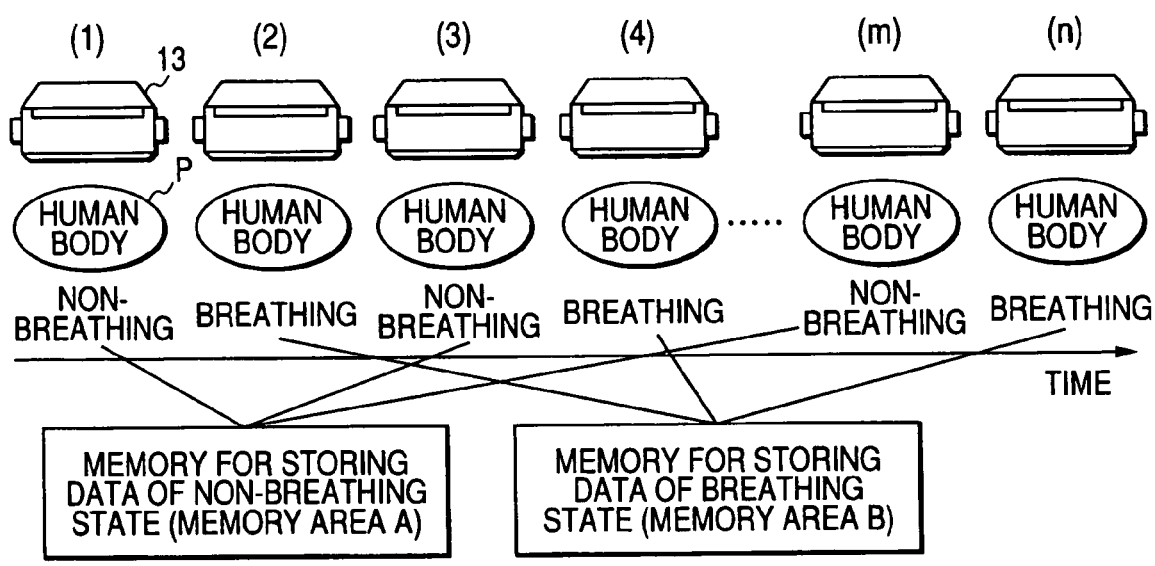
FIG. 7 is a diagram for explaining the concept of non-breathing and breathing in the data acquisition control of the planar method as shown in FIG. 6.

The concept of the above data acquisitions of the planar method applying the "intermittent data acquisition method" is shown in schematical fashion in FIG. 7. In the course of the data acquisitions, the patient P pushes the manipulation switch 31 at his/her own will and simultaneously starts the breath holding, and he/she pushes the manipulation switch 31 again and interrupts the breath holding. The acquired data in the temporary breath stop periods (in the non-breathing state) are accumulated in the memory area A by iterating such operations, so that a projection image is generated by a data processing unit 22 being an image generation unit, by using the projection data in the memory area A (refer to (1), (3), . . . and (m) in FIG. 7).

In this manner, according to this embodiment, as in the first embodiment described before, the projection image of high image quality can be obtained by excluding the factors of image quality degradation ascribable to bodily motions, substantially without fail. Moreover, since the patient P can conduct the breath holding at his/her own will, the burden of the breath holding on the patient P can be remarkably relieved. Besides, since the acquired data of the non-breathing state and those of the breathing state are stored separately in accordance with the switch signals from the beginning, processing such as flag check is dispensed with at the time of the projection-image generation, to bring forth the advantage that the generation process is simplified more.

4. Modification to Second Embodiment

Figure 8:
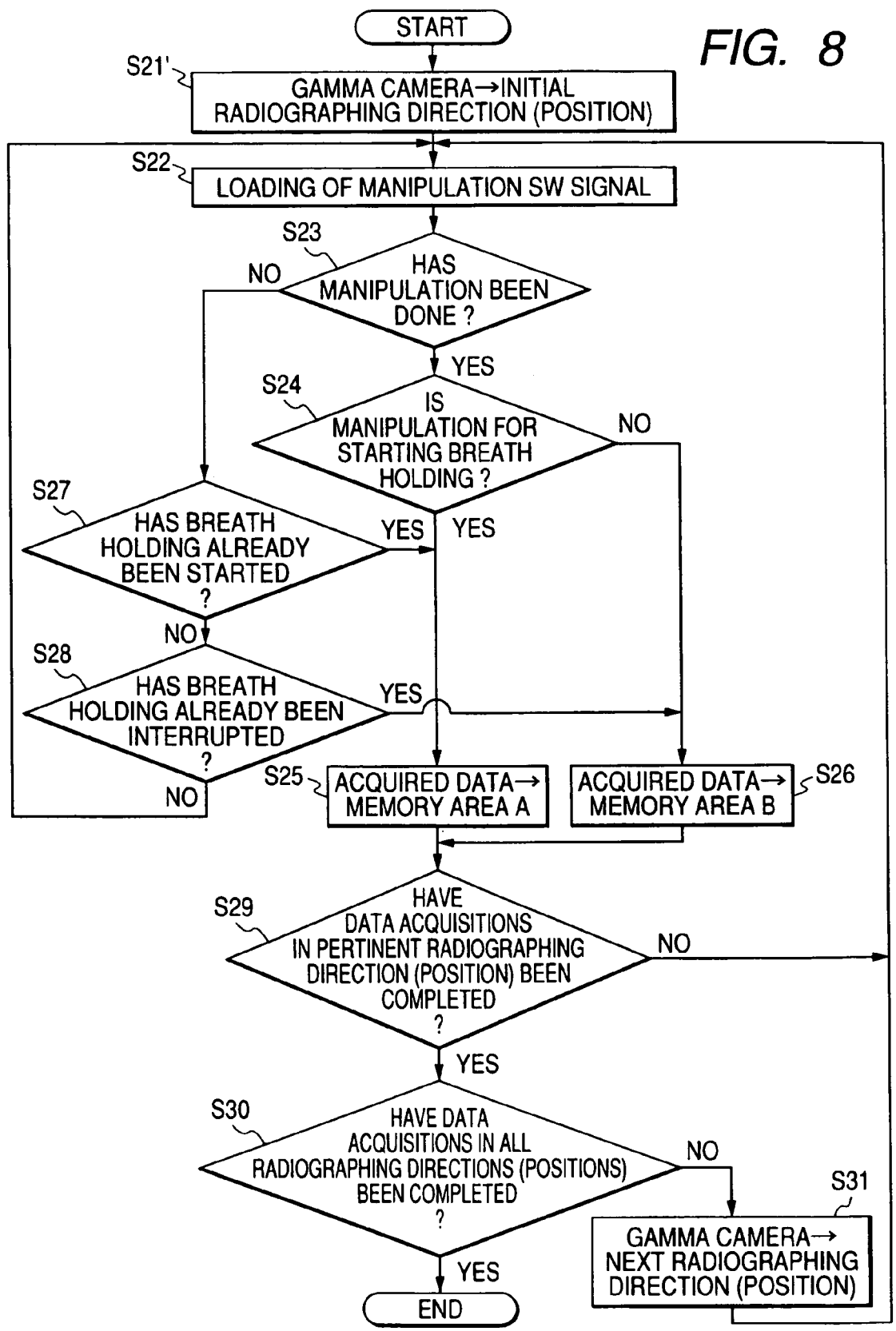
FIG. 8 is a flow chart showing the outline of the data acquisition control of a SPECT method applying the "intermittent data acquisition method" as is performed in a modification to the second embodiment.

FIG. 8 shows a modification to the second embodiment. A flow chart in FIG. 8 shows the process of the "intermittent data acquisition method" applied to a SPECT method as has expanded the process shown in FIG. 6. In FIG. 8, steps which execute processing identical or equivalent to the processing of the foregoing steps in FIG. 6 are denoted by the same signs.

In the "intermittent data acquisition method" applied to the SPECT method, the gamma camera 13 is first located in an initial radiographing direction (position) by the system controller 25 (step S21'), and the same processing steps as in FIG. 6 are thereafter executed (steps S22-S29). Further, whether or not data acquisitions in all radiographing directions (positions) have been completed is judged by the system controller 25 (step S30). In a case where the judgment becomes "NO", the gamma camera 13 is spatially moved into the next radiographing direction (position), and similar data acquisitions are iterated (step S31).

Therefore, when the data acquisitions have been completed in all the radiographing directions (positions), a tomogram is reconstructed by the data processing unit 22. Accordingly, the SPECT method based on the "intermittent data acquisition method" enjoying the same advantages as in the planar method is performed.

Incidentally, the planar method and the SPECT method applying the "intermittent data acquisition method" as described above can be similarly carried out in a nuclear medical diagnostic equipment which performs tomography called "positron ECT (positron emission computed tomography: PET)", and a data acquisition method for the equipment.

5. Third Embodiment

Next, the third embodiment of the invention will be described with reference to FIGS. 9-11.

A nuclear medical diagnostic equipment according to the third embodiment concerns a construction which performs a SPECT method based on the "intermittent data acquisition method". In particular, this embodiment features that, when a gamma camera 13 is rotated round a patient P stepwise so as to acquire data in each of a plurality of radiographing directions (positions), breathings and temporary breath stops based on the breath holdings are alternately iterated. On this occasion, the plurality of radio graphing directions (positions) are defined so as to double those of the ordinary SPECT method in number (for example, 3 degrees per step, and 10-15 seconds in terms of an acquisition time period), and such acquisitions are iterated (for example, iterated 60 times). The outline of the process of this embodiment is shown in FIG. 9. Incidentally, the hardware architecture of the nuclear medical diagnostic equipment according to this embodiment is the same as shown in FIG. 1.

Figure 9:
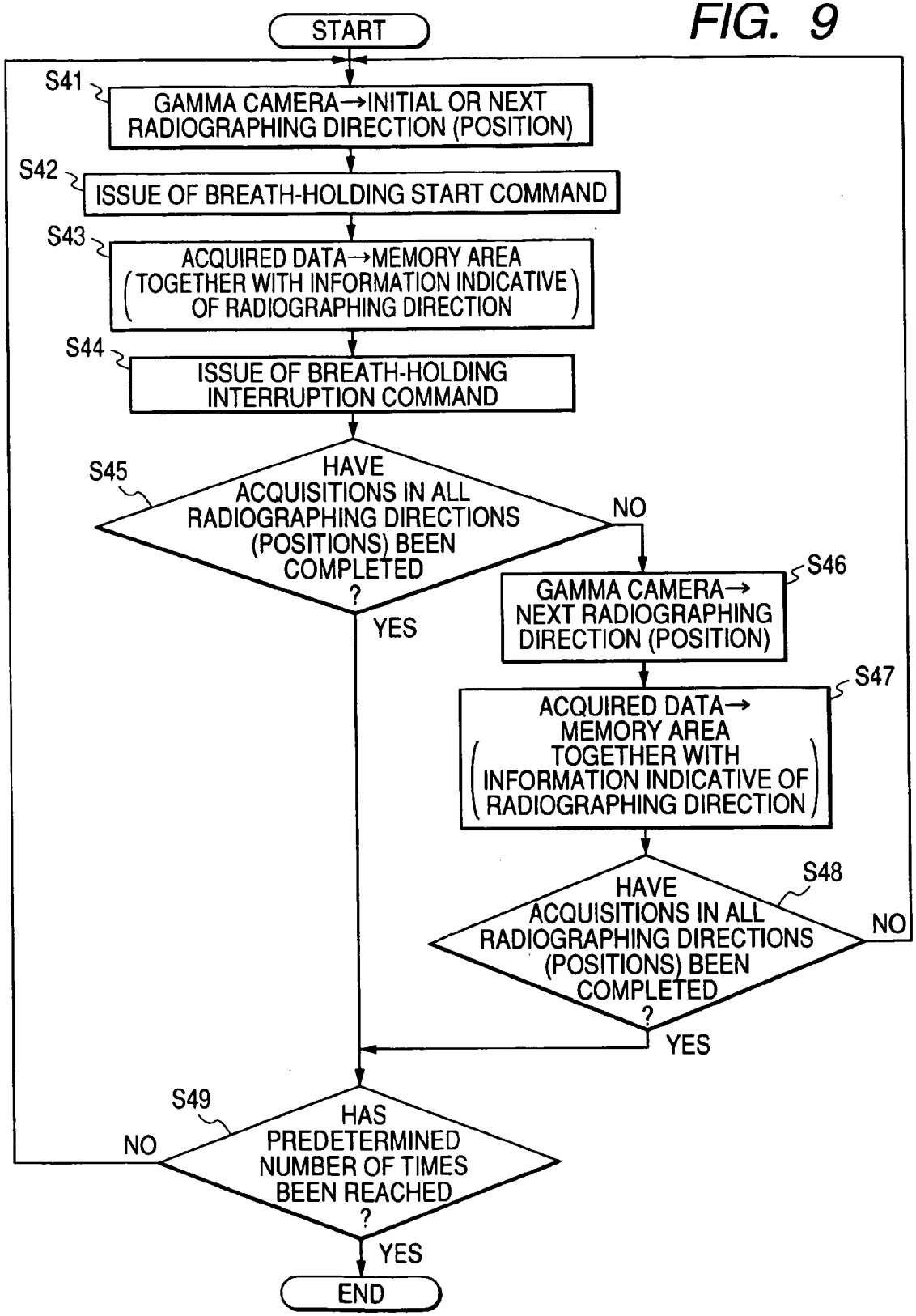
FIG. 9 is a flow chart showing the outline of the data acquisition control of a SPECT method applying an "intermittent data acquisition method" as is performed in the third embodiment.

As shown in FIG. 9, a system controller 25 first locates the gamma camera 13 into an initial radiographing direction (position) (step S41), a command for the start of breath holding is given in terms of, for example, automatic voice by the system controller 25, a vocal message generation unit 29 and a loudspeaker 15 which function as a breath-holding control unit (step S42), and acquired data are recorded with identification information based on marking, for a time period t1 (step S43). Subsequently, a command for the interruption of the breath holding is given in terms of, for example, automatic voice (step S44). That is, in data acquisition in the current radiographing direction (position), the data are acquired in a state where the patient P has conducted breath holding to temporarily stop his/her breath.

Further, whether or not data acquisitions in all radiographing directions (positions) have been completed is judged (step S45). In a case where the data acquisitions have not been completed yet, the system controller 25 moves the gamma camera 13 into the next radiographing direction (position) (step S46).

In the new radiographing direction (position) after the movement, acquired data are merely recorded without giving commands for the start and interruption of breath holding, this time (step S47). Therefore, data acquisition in this radiographing direction (position) proceeds in a state where the patient P respires freely. Thereafter, whether or not the data acquisitions in all the radiographing directions (positions)

have been completed is judged again (step S48). In a case where the judgment is "NO", the routine returns to the foregoing step S42, at which the gamma camera 13 is altered into the next radiographing direction (position), and data are similarly acquired in this radiographing direction (position).

On the other hand, in a case where the judgment at the step S45 or S48 is "YES", that is, where it is judged that the data acquisitions in all the radiographing directions (positions) have been completed, the system controller 25 further judges whether or not the number of times of data acquisitions in the series of all the radiographing directions (positions) has reached a predetermined iteration number of times (for example, 60 times) (step S49). In a case where the judgment at the step S49 becomes "NO", that is, where the predetermined iteration number has not been reached yet, the routine returns to the first step S42 so as to iterate the processing. When the judgment at the step S49 becomes "YES", the data acquisitions are completed, and a tomogram is reconstructed by a data processing unit 22 being an image generation unit.

Figure 10:
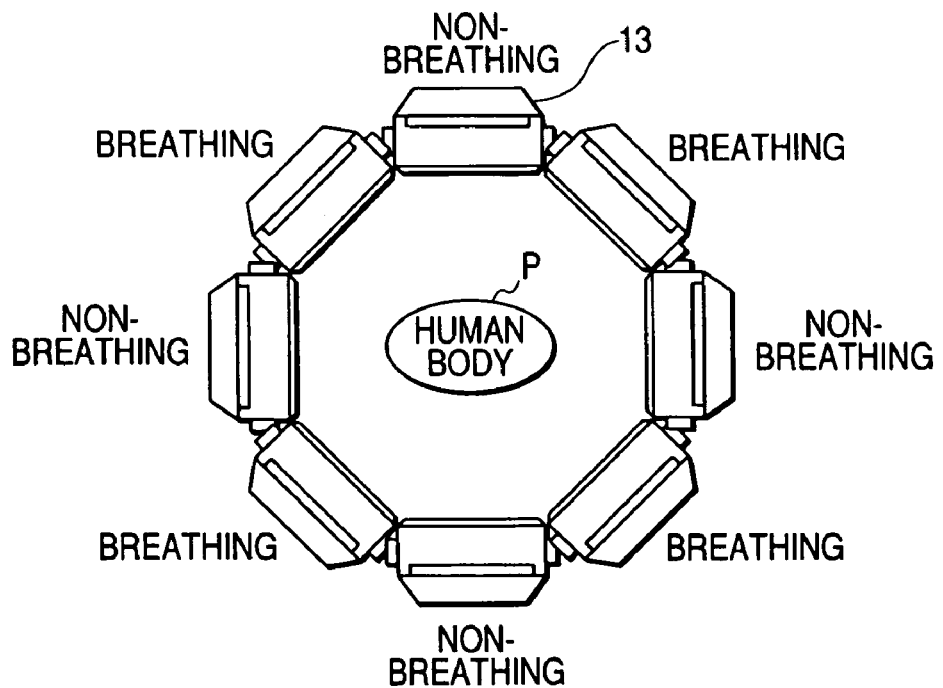
FIG. 10 is an explanatory view showing the outline of the data acquisition control of the SPECT method applying the "intermittent data acquisition method" as is performed in the third embodiment.
Figure 11:
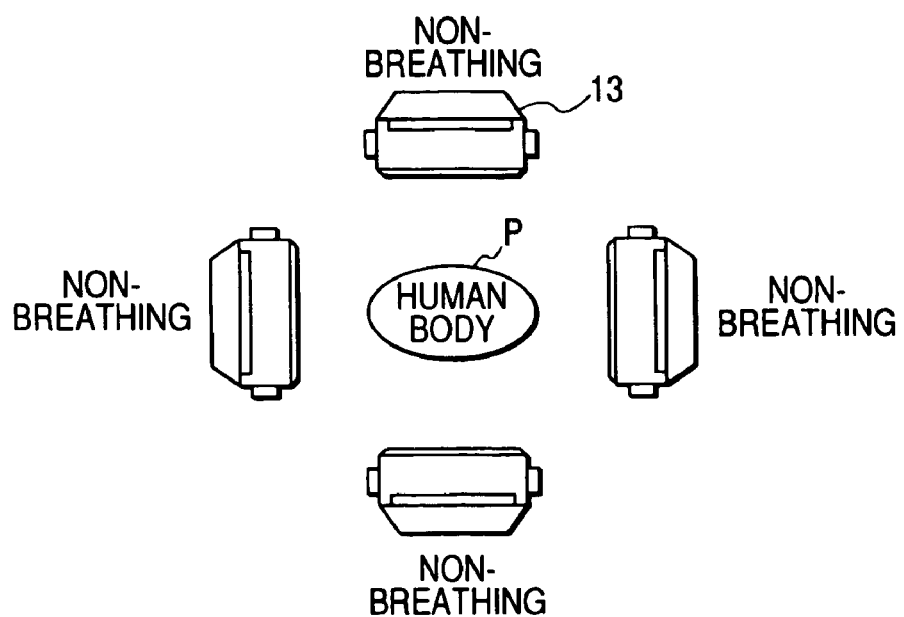
FIG. 11 is a diagram showing data acquisitions which are employed for the reconstruction of a tomogram, among data acquisitions shown in FIG. 10.

As shown in schematical fashion in FIG. 10, therefore, the SPECT method based on the "intermittent data acquisition method" is such that the "breath stop" is conducted every second radiographing direction (position), and that the data are acquired in the state of the "breath stop" (non-breathing state) and the state of "taking breath" (breathing state), respectively. As shown in schematical fashion in FIG. 11, accordingly, the data acquired in the "breath stop" one of the states are extracted on the basis of the identification information, and the tomogram is reconstructed using the acquired data. Therefore, the patient P may conduct the breath holding in compliance with, for example, the automatic voice for a reasonable time period every second one of the radiographing directions (positions) altered regularly, and he/she can hold his/her breath more reliably, so that the image quality degradation of the reconstructed image attributed to bodily motions can be prevented.

Incidentally, the SPECT method applying the "intermittent data acquisition method" as described above can be similarly carried out in a nuclear medical diagnostic equipment which performs tomography called "positron ECT (positron emission computed tomography: PET)", and a data acquisition method for the equipment.

Incidentally, the patient P need not always be given the instructions of the timings of the start and interruption of the breath holding by the above construction based on the automatic voice generation (or automatic voice), but an operator may well give vocal instructions through a microphone or the like while watching the state of the patient P. Alternatively, character displays may well be presented by a panel, or light may well be turned ON and OFF for the instructions. That is, a respiration identification unit can be constituted by any desired constituent such as the microphone or the panel which is disposed in addition to, or in place of, the loudspeaker.

6. Fourth Embodiment

Next, the fourth embodiment of the invention will be described with reference to FIGS. 12-17.

A nuclear medical diagnostic equipment according to the fourth embodiment differs from the nuclear medical diagnostic equipment in the first to third embodiments and the modifications thereof, in a method of reconstructing or generating a tomogram or projection image by a data processing unit 22 on the basis of projection data respectively obtained in the non-breathing state and breathing state of a patient P in an identifiable manner, and a method of displaying the tomogram on a display unit 26.

Since the remaining construction and operation are substantially the same as in the nuclear medical diagnostic equipments in the first to third embodiments and the modifications thereof, only a functional block diagram of the data processing unit 22 and relevant constituents shall be shown, and identical signs shall be assigned to the same constituents and omitted from description. Besides, although the case of reconstructing the tomogram will be described here, the same holds true of the case of generating the projection image.

Figure 12:
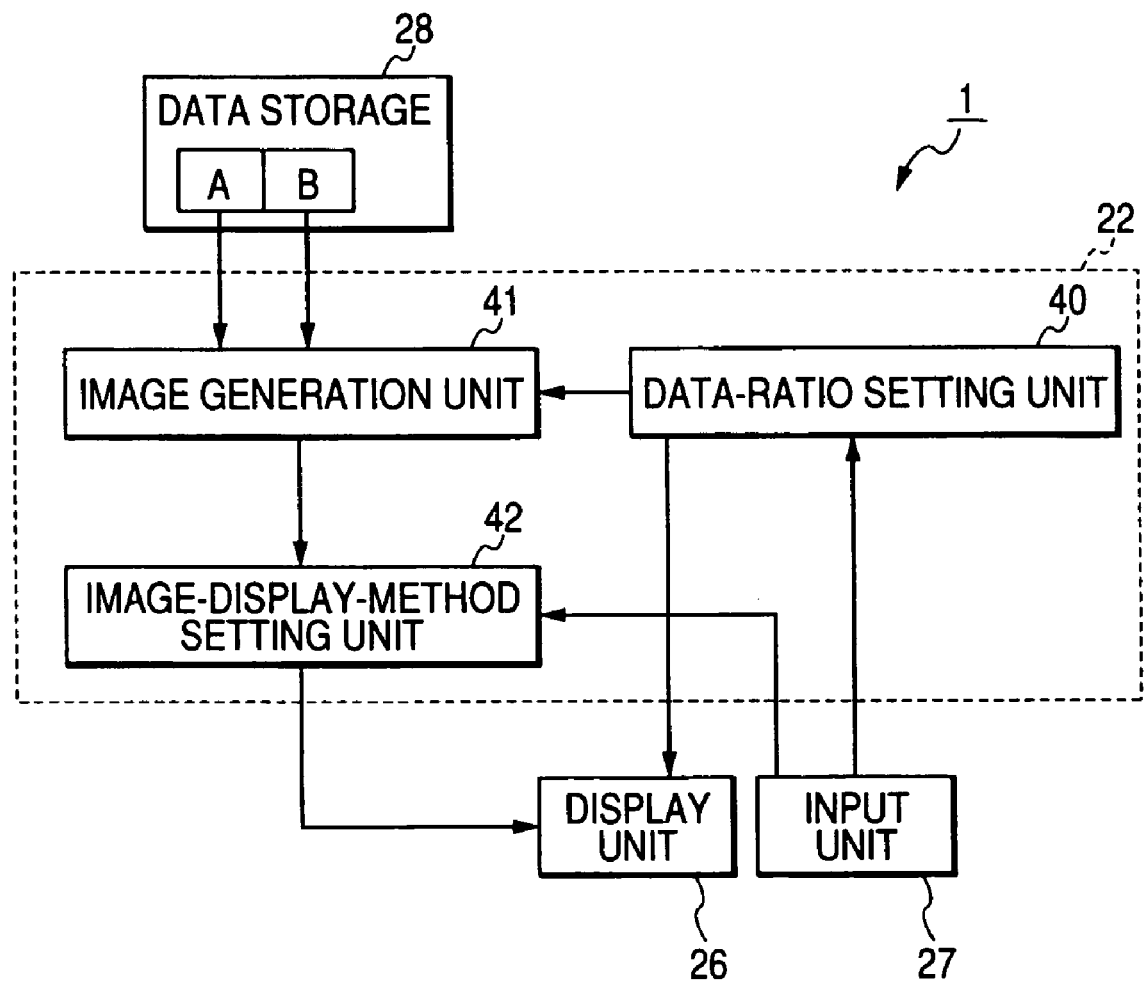
FIG. 12 is a functional block diagram showing the outline of a nuclear medical diagnostic equipment according to the fourth embodiment of the invention.

FIG. 12 is the functional block diagram showing the outline of the nuclear medical diagnostic equipment according to the fourth embodiment of the invention.

The data processing unit 22 of the nuclear medical diagnostic equipment according to the fourth embodiment operates by having programs loaded into an arithmetic unit, thereby to function as a data-ratio setting unit 40, an image generation unit 41 and an image-display-method setting unit 42. Herein, the data-ratio setting unit 40, image generation unit 41 and image-display-method setting unit 42 may well be wholly or partly constructed of circuitry.

In a data recording unit 28, the projection data respectively obtained in the non-breathing state and breathing state of the patient P are saved in the identifiable manner. By way of example, the data recording unit 28 includes a memory M divided into memory areas A and B, and the projection data obtained in the non-breathing state are saved in the memory area A, while the projection data obtained in the breathing state are saved in the memory area B. However, identification information may well be affixed to the projection data by marking, instead of the division of the memory M as in the nuclear medical diagnostic equipment in the first embodiment shown in FIG. 1.

The image generation unit 41 has the function of reconstructing the tomogram by using the projection data respectively obtained in both the non-breathing state and the breathing state. On this occasion, the projection data obtained in the breathing state can be employed for the reconstruction of the tomogram at a rate previously set by the data-ratio setting unit 40, without employing all of them.

By the way, in reconstructing the tomogram, the projection data obtained in the breathing state are added to the projection data obtained in the non-breathing state. In this regard, after tomograms have been once generated, the tomogram obtained in the breathing state may well be added to the tomogram obtained in the non-breathing state.

The data-ratio setting unit 40 has the function of setting the rate at which the image generation unit 41 employs the projection data obtained in the breathing state, for the reconstruction of the tomogram, so as to give the command of the rate to the image generation unit 41. A user can give an instruction for the rate of the projection data to be employed for the reconstruction of the tomogram, at will by giving information to the data-ratio setting unit 40 through an input unit 27. Besides, the information necessary for setting the rate of the projection data to be employed for the reconstruction of the tomogram is delivered from the data-ratio setting unit 40 to the display unit 26 so as to be displayed on this display unit.

The image-display-method setting unit 42 has the function of determining whether a plurality of tomograms which have been reconstructed at the different rates of the projection data by the image generation unit 41 are to be displayed while being changed-over or to be displayed side by side, in compliance with a command from the input unit 27, so as to feed the tomograms to the display unit 26 in accordance with the determined image display method and to display them by the desired display method.

Next, there will be described the steps of procedure for the reconstruction of the tomogram by the nuclear medical diagnostic equipment according to the fourth embodiment.

Figure 13:
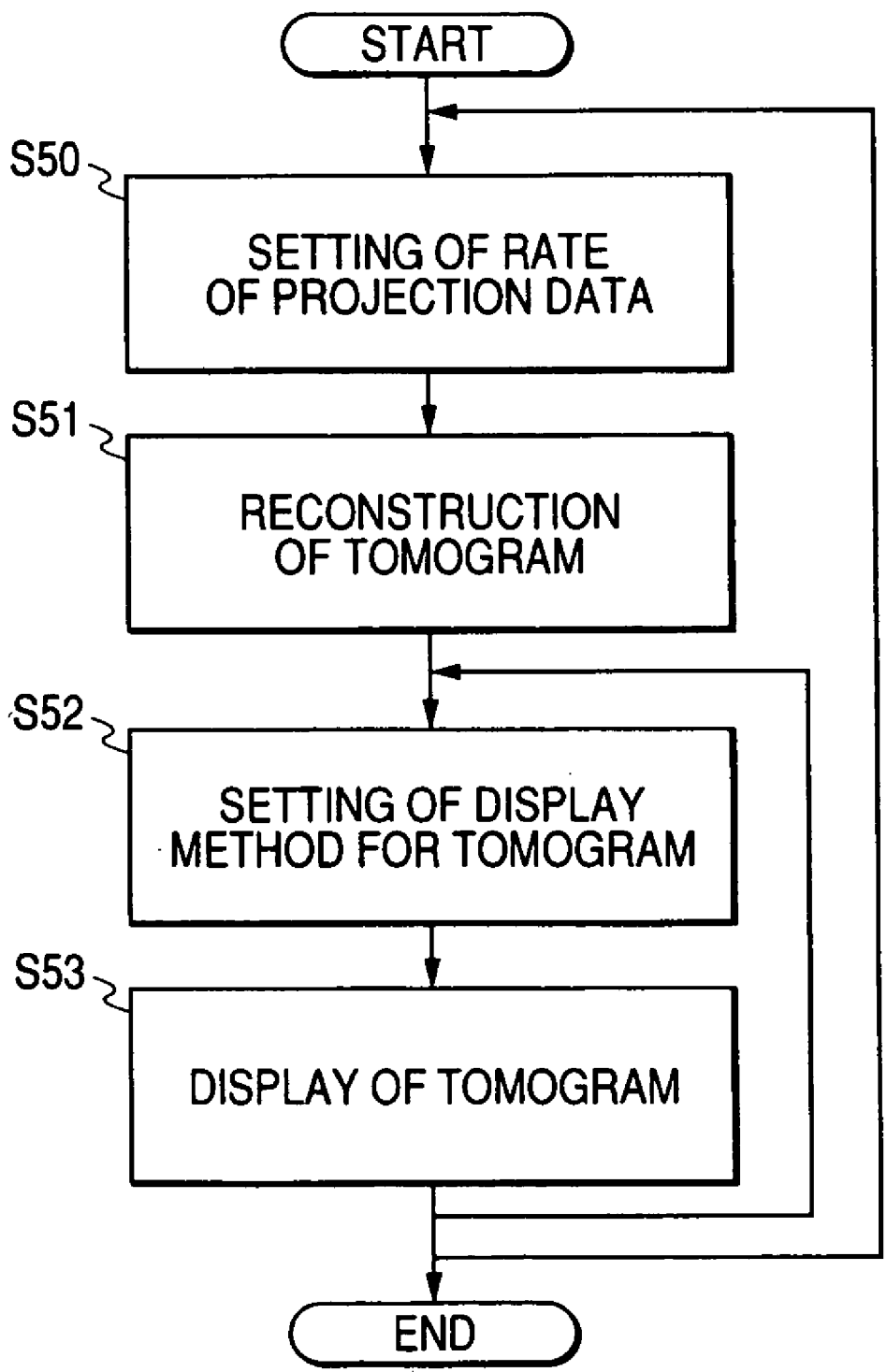
FIG. 13 is a flow chart showing an example of the steps of procedure for the reconstruction of a tomogram by the nuclear medical diagnostic equipment according to the fourth embodiment as shown in FIG. 12.

FIG. 13 is a flow chart showing an example of the steps of procedure for the reconstruction of the tomogram by the nuclear medical diagnostic equipment according to the fourth embodiment as shown in FIG. 12.

First, the projection data obtained in the non-breathing state and breathing state of the patient P are respectively saved in the memory areas A and B of the memory M of the data recording unit 28 in an identifiable manner beforehand.

Besides, at a step S50, the rate of projection data to be employed for the reconstruction of a tomogram, among projection data obtained in the breathing state, is set. More specifically, first of all, in setting the rate of the projection data, information for receiving an instruction from the input unit 27 is given to the display unit 26 by the data-ratio setting unit 40. Therefore, a scroll bar, for example, is displayed on the display unit 26.

Accordingly, the user can set the rate of the projection data for use in the reconstruction of the tomogram, at will within a range from 0% through 100%, in such a way that he/she moves the scroll bar by manipulating the input unit 27 such as mouse. Further, the manipulation information of the input unit 27 is sent to the data-ratio setting unit 40, and the rate of the projection data is set. In addition, the set rate of the projection data is delivered from the data-ratio setting unit 40 to the image generation unit 41.

Subsequently, at a step S51, the image generation unit 41 reconstructs the tomogram by loading the projection data of the non-breathing state and breathing state saved in the memory M of the data recording unit 28, in accordance with the rate of the projection data as received from the data-ratio setting unit 40. In a case, for example, where the rate of the projection data for use in there construction of the tomogram, among the projection data obtained in the breathing state, is set at 50%, the tomogram is reconstructed by loading 50% of the projection data of the breathing state and 100% of the projection data of the non-breathing state from the data recording unit 28.

Subsequently, at a step S52, an instruction for displaying the reconstructed tomogram is given from the input unit 27 to the image-display-method setting unit 42. Accordingly, a display method is set so as to display the single tomogram reconstructed using the projection data of the designated rate.

Subsequently, at a step S53, the image-display-method setting unit 42 receives the tomogram from the image generation unit 41 and delivers the tomogram to the display unit 26 so as to display this tomogram in accordance with the set image display method.

Figure 14:
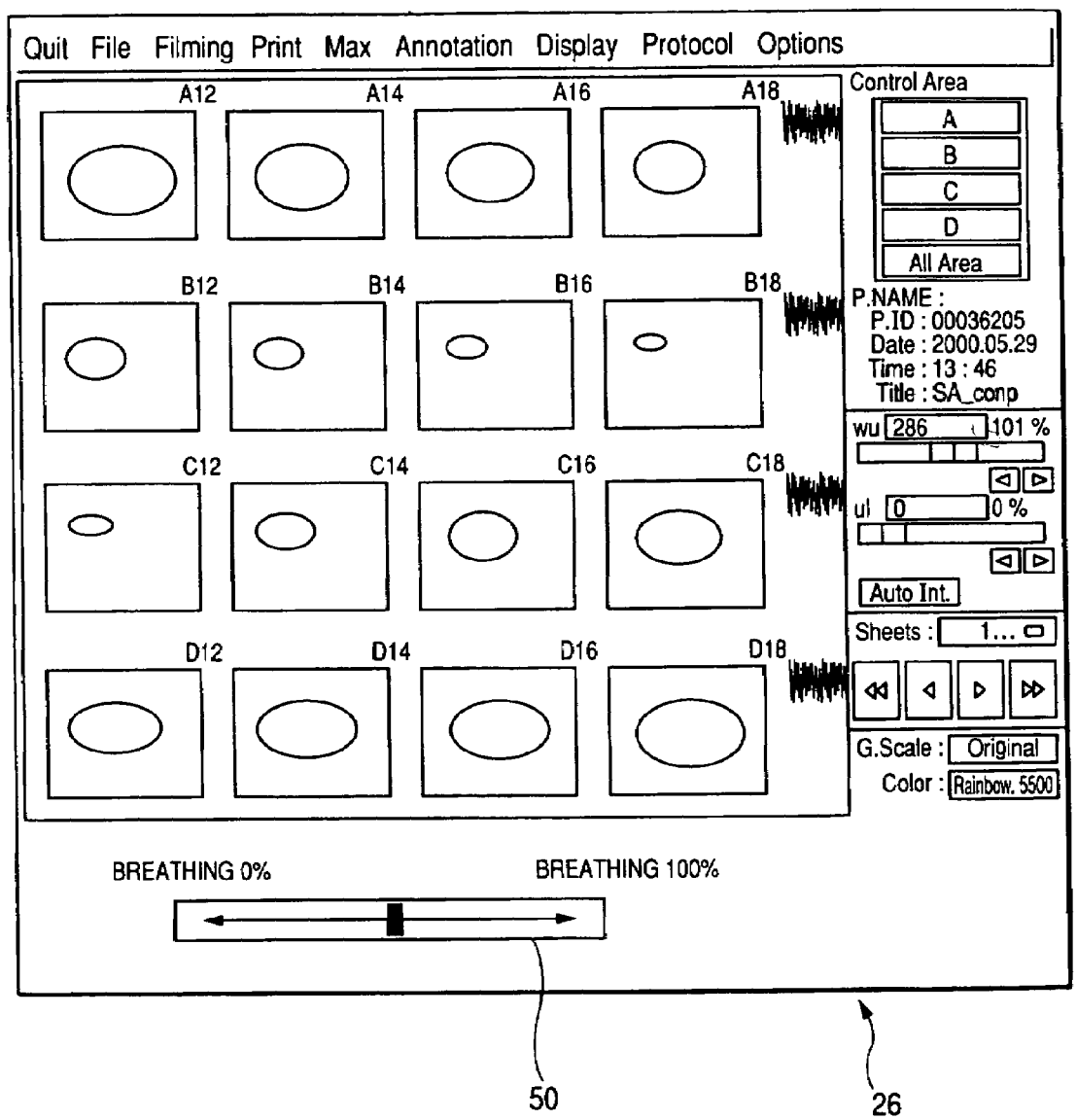
FIG. 14 is a diagram showing display examples of the tomograms which have been reconstructed by the nuclear medical diagnostic equipment according to the fourth embodiment as shown in FIG. 12.

FIG. 14 is a diagram showing a display example of tomograms which have been reconstructed by the nuclear medical diagnostic equipment according to the fourth embodiment as shown in FIG. 12.

As shown in FIG. 14, the rate of projection data for use in the reconstruction of the tomogram, in projection data obtained in the breathing state, can be set by manipulating the scroll bar 50 through the input unit 27. Herein, the projection data of the set rate are employed for the reconstruction of the tomogram and are displayed on the display unit 26.

Besides, various buttons and scroll bars which are usually displayed by GUI (Graphical User Interface) technology are displayed on the display unit 26. By way of example, four sorts of buttons A, B, C and D for setting the layout of image display are disposed, and the images of all areas can be displayed by selecting the "All Area" button. Also, a button for scrolling a display frame, and a part for setting a color scale are disposed in addition to the scroll bar for setting the upper limit value and lower limit value of the rate of pixel values to-be-displayed.

In this manner, the rate of the projection data for use in the reconstruction of the tomogram is adjusted, whereby the sensitivity and positional resolution of the tomogram can be set at desired values according to a clinical purpose.

Figure 15:
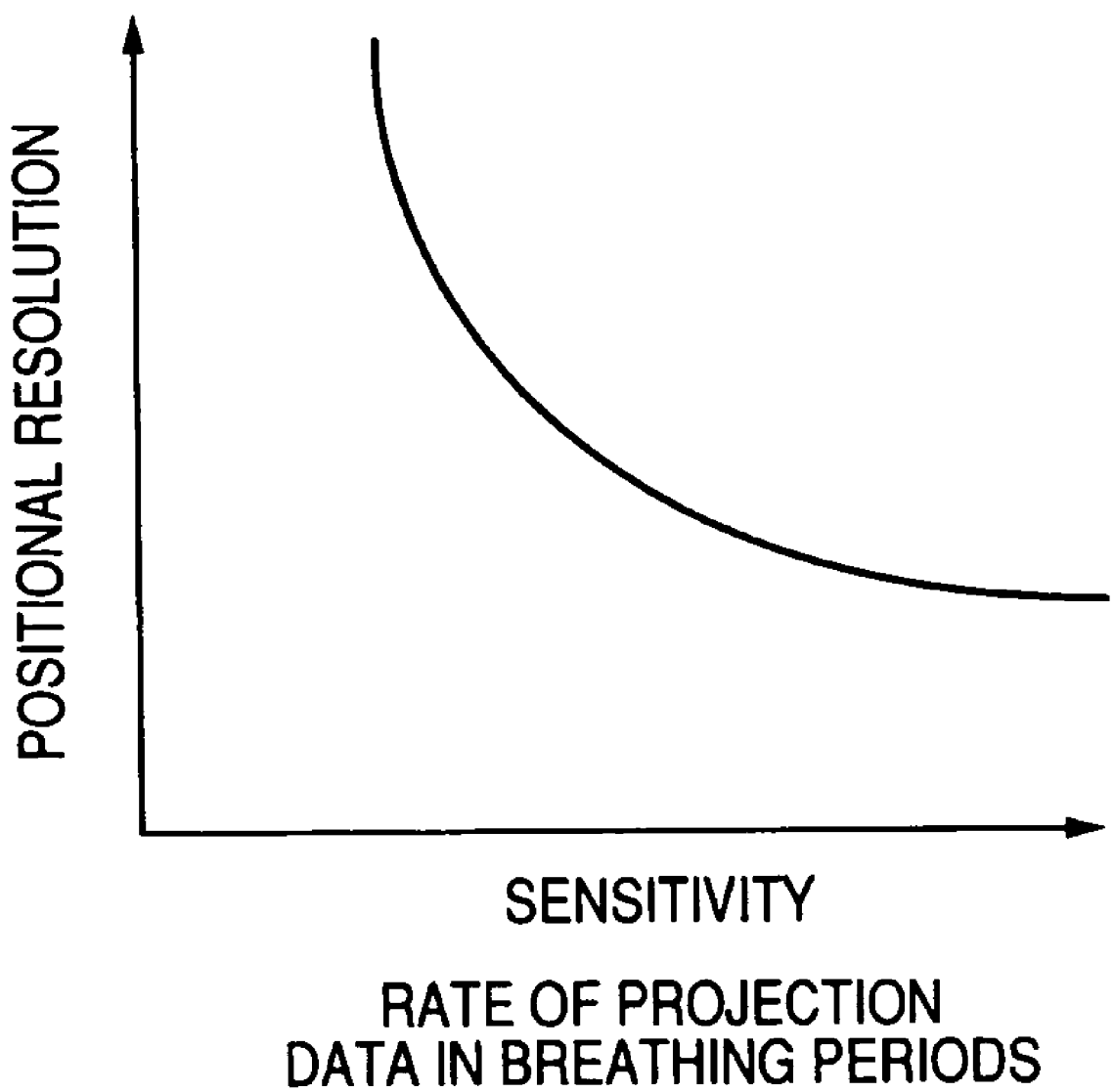
FIG. 15 is a graph showing in simplified fashion the relationship between the positional resolution and sensitivity of the tomograms which have been reconstructed by the nuclear medical diagnostic equipment according to the fourth embodiment as shown in FIG. 12.

FIG. 15 is a graph showing in simplified fashion the relationship between the positional resolution and sensitivity of the tomograms which have been reconstructed by the nuclear medical diagnostic equipment according to the fourth embodiment as shown in FIG. 12.

In FIG. 15, the axis of abscissas represents the sensitivity of the tomogram, while the axis of ordinates represents the positional resolution of the tomogram.

Assuming that an image be generated using only data acquired in non-breathing periods, the degradations of the positional resolution and contrast of the image attributed to the bodily motions of a patient can be suppressed. Since, however, data are not acquired in breathing periods, the number of samplings decreases, with the result that the smoothness, namely, sensitivity of the image degrades. Accordingly, the positional resolution and sensitivity of the image are in trade-off relationship as indicated by a solid line in FIG. 15. That is, the positional resolution of the tomogram is enhanced more as the projection data in the breathing periods of the patient are removed more from the projection data for the tomogram generation, while the sensitivity of the tomogram is enhanced more as the projection data in the breathing periods of the patient are employed more as the data for the tomogram generation.

In the nuclear medical diagnostic equipments in the first to third embodiments and the modifications thereof as described before, the enhancement of the positional resolution is principally aimed at, and only the projection data in the non-breathing state are employed for the reconstruction of the tomogram. In some clinical purposes, however, the enhancement of the sensitivity of the tomogram is important rather than the enhancement of the positional resolution or contrast thereof.

Besides, a nuclear medical diagnostic equipment usually radiographs a patient P in 60-90 directions, and the necessary number of radiographing times is determined in accordance with the number of gamma cameras 13 being detectors. In a case, for example, where the patient P is radiographed in 60 directions by employing two gamma cameras 13, 60/2=30 times of radiographing operations are required, and a time period of about 10-20 seconds is expended on the radiographing operation in one direction.

Therefore, if only the projection data in the non-breathing state are used for the reconstruction of the tomogram, data acquired for about 20 seconds after the breath stop are not used for the reconstruction of the tomogram. Especially in a case where the number of the gamma cameras 13 is small, the loss of a radiographing time period increases, and the acquisition counts of the data decrease. This might lead to the degradation of the sensitivity.

The use of the projection data in the breathing state for the reconstruction of the tomogram is sometimes desirable in order that, even in such a case, the degradation of the sensitivity may be suppressed by increasing the number of samplings to some extent, with the necessary positional resolution kept.

Therefore, the user can set the ratio of the projection data in the breathing state through the manipulation of the input unit 27 so that the tomogram may come to have the desired sensitivity. As a result, the tomogram can be obtained at the higher positional resolution and sensitivity in accordance with the clinical purpose, and besides, the projection data obtained in the breathing state can be effectively utilized.

Further, the ratio of the projection data in the breathing state can be iteratively set at will at the step S50 so as to update the display of the tomogram.

Besides, at the step S52, the display method for the tomogram can be altered. By way of example, a plurality of tomograms are reconstructed by setting different rates for the projection data, and an instruction is given to the image-display-method setting unit 42 through the input unit 27, whereby the individual tomograms can be displayed side by side.

Figure 16:
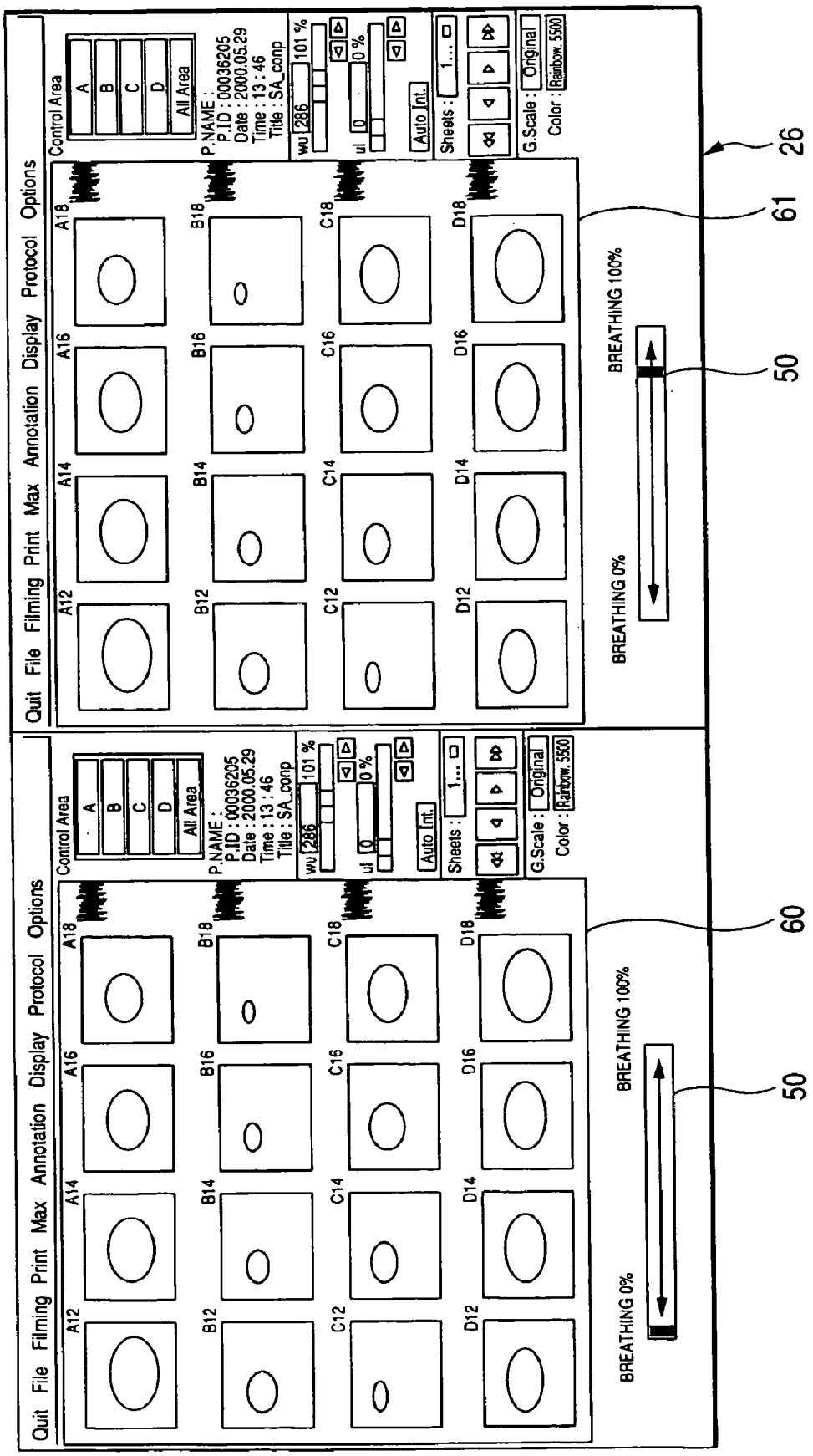
FIG. 16 is a diagram showing an example in which the plurality of tomograms reconstructed by the nuclear medical diagnostic equipment according to the fourth embodiment as shown in FIG. 12 are simultaneously displayed.

FIG. 16 is a diagram showing an example in which the plurality of tomograms reconstructed by the nuclear medical diagnostic equipment according to the fourth embodiment as shown in FIG. 12 are simultaneously displayed.

As shown in FIG. 16 by way of example, the rate of the projection data in the breathing state is set at 0%, and the first tomograms 60 are reconstructed using only the projection data in the non-breathing state, while the rate of the projection data in the breathing state is set at 80%, and the second tomograms 61 are reconstructed using the projection data in both the non-breathing state and the breathing state, whereupon both the first and second tomograms 60 and 61 can be displayed on the display unit 26 side by side.

When the tomograms at different sensitivities and positional resolutions a redisplayed side by side in this manner, the diagnosis is facilitated still more.

Besides, a method of setting the rates of the projection data is at will, and the rates can be set, not only by scroll bars 50, but also in terms of, for example, numerical values. Further, it is possible to adopt a construction in which a plurality of tomograms are reconstructed by setting different rates for the projection data, and in which the individual tomograms are displayed while being changed-over.

Figure 17:
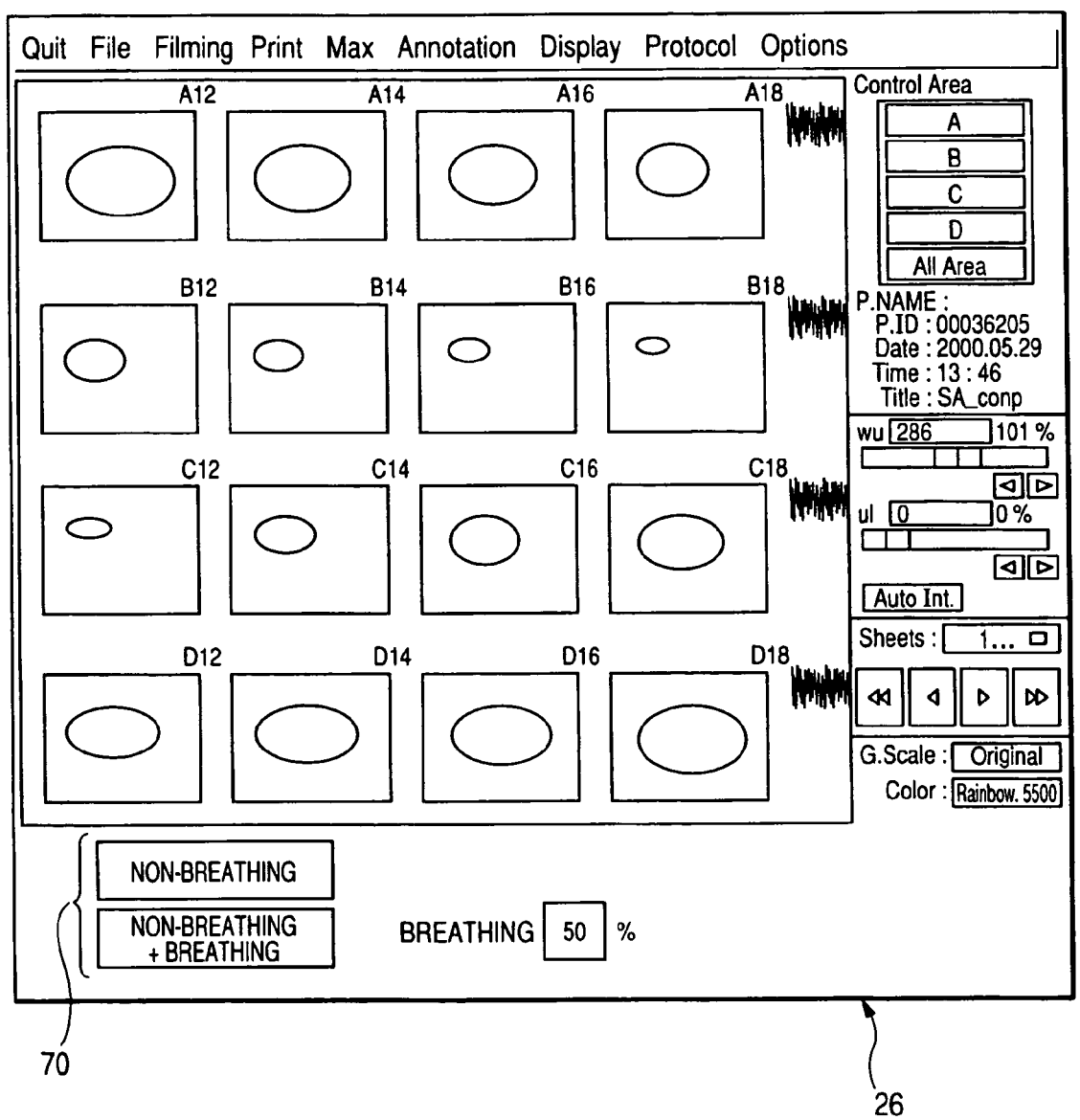
FIG. 17 is a diagram showing another display example of the tomograms which have been reconstructed by the nuclear medical diagnostic equipment according to the fourth embodiment as shown in FIG. 12.

FIG. 17 is a diagram showing another display example of the tomograms which have been reconstructed by the nuclear medical diagnostic equipment according to the fourth embodiment as shown in FIG. 12.

As shown in FIG. 17 byway of example, the tomograms whose positional resolutions are enhanced are reconstructed using only the projection data obtained in the non-breathing state, while the tomograms whose sensitivity degradations are suppressed are reconstructed by setting the rate of the projection data obtained in the breathing state, as the numerical value, whereupon the displays of the tomograms can be changed-over with a button 70 which selects the tomograms to be displayed on the display unit 26. In this case, selection information for the button 70 is sent to the image-display-method setting unit 42 through the input unit 27, and the selected tomograms are delivered from the image-display-method setting unit 42 to the display unit 26 so as to be displayed on this display unit.

According to such a display method for the tomograms, only the tomograms of high necessity can be reconstructed in a short time and displayed on the display unit 26 by lesser processings.

The present invention as thus far described is not restricted to the foregoing embodiments and modifications, but it can be further modified or expanded into appropriate aspects by employing hitherto-known constructions, within a scope not departing from the purport of the invention as defined in the appended claims. Moreover, all or some of the constituents of the nuclear medical diagnostic equipments in the embodiments and modifications can be combined with one another into multifunctional constructions.

What is claimed is:

1. A nuclear medical diagnostic equipment including a radiation detector, wherein radiation which is emitted by a nuclide administered into a body of a patient is detected as projection data by the radiation detector, and an image which indicates a distribution of the nuclide within the body of the patient is obtained on the basis of the projection data, comprising:

a rotation unit which rotates the radiation detector around the patient;

a respiration identification unit which identifies breathing of the patient and non-breathing thereof based on breath holding;

a data storage unit in which the radiation detection data is acquired by said radiation detector, with iterating an instruction of the breathing and an instruction of the non-breathing by breath holding alternately to the patient are stored in an identifiable manner on the basis of a result of the identification by said respiration identification unit; and an image generation unit which generates a first image by using only radiation detection data acquired in a state of non-breathing among the radiation detection data stored in said data storage unit on the basis of the result of the identification by said respiration identification unit and a second image by using radiation detection data acquired in the state of non-breathing and a state of breathing, wherein said radiation detector is configured to acquire data at both breathing periods and at non-breathing periods, the breathing and the non-breathing periods are associated to alternating radiographic directions, that are arranged at regular sectional intervals circularly around the patient, and the rotation unit is configured to stop the rotation of the radiation detector during the acquisition of data at the respective alternating radiographic directions.

2. A nuclear medical diagnostic equipment as defined in claim 1, wherein said respiration identification unit includes a command unit which gives commands for time periods of the breath holdings, and an acquisition unit which acquires the projection data detected by said radiation detector in synchronism with the breath holding time periods commanded by said command unit.

3. A nuclear medical diagnostic equipment as defined in claim 1, wherein said respiration identification unit includes a command unit which gives commands for time periods of the breath holdings, an acquisition unit which acquires the projection data detected by said radiation detector in synchronism with the breath holding time periods commanded by said command unit, and an addition unit which adds up the projection data acquired in only the breath holding time periods by said acquisition unit.

4. A nuclear medical diagnostic equipment as defined in claim 1, wherein said respiration identification unit includes a signal generation unit which generates signals respectively indicating a start and an end of each of the breath holdings, and an acquisition unit which acquires the projection data detected by said radiation detector, in accordance with the signals generated by said signal generation unit.

5. A nuclear medical diagnostic equipment as defined in claim 4, wherein said signal generation unit is a switch which can be manipulated by the patient.

6. A nuclear medical diagnostic equipment as defined in claim 4, wherein said signal generation unit is a switch which can be manipulated by the patient, and said data storage unit records the projection data in different memory areas corresponding respectively to the periods for which said signal generation unit has generated the signals respectively indicating the starts and ends of the breath holdings, and to the other periods.

7. A nuclear medical diagnostic equipment as defined in claim 1, wherein said radiation detector is fixed at a position in a predetermined radiographic direction so as to detect the projection data.

8. A nuclear medical diagnostic equipment as defined in claim 1, wherein said radiation detector is successively moved to positions in a plurality of radiographic directions so as to detect the projection data at the positions in the respective radiographic directions.

9. A nuclear medical diagnostic equipment as defined in claim 8, wherein said nuclear medical diagnostic equipment is an equipment which performs tomography called either of "single photon emission computed tomography" or "positron emission computed tomography".

10. A nuclear medical diagnostic equipment as defined in claim 1, wherein:
said radiation detector is successively moved to positions in a plurality of radiographic directions so as to detect the projection data at the respective positions in the radiographic directions; and
said respiration identification unit includes a breath-holding control unit which causes the patient to conduct the breath holdings and stops of the breath holdings alternately and iteratively at the respective positions in the plurality of radiographic directions, and it acquires the projection data acquired by said radiation detector so as to supply the acquired projection data for the generation of the image, during only periods of the breath holdings based on said breath-holding control unit.

11. A nuclear medical diagnostic equipment as defined in claim 1, further comprising an image-display-method setting unit which displays the first image and the second image on a display unit simultaneously.

12. A nuclear medical diagnostic equipment as defined in claim 1, wherein said image generation unit includes a data-ratio setting unit which sets a rate of the radiation detection data for use in the image generation, in the radiation detection data acquired in a state of the breathing, and it generates an image by using the radiation detection data at the rate set by said data-ratio setting unit.

13. A nuclear medical diagnostic equipment wherein radiation which is emitted by a nuclide administered into a body of a patient is detected as projection data by a radiation detector, and an image which indicates a distribution of the nuclide within the body of the patient is obtained on the basis of the projection data, comprising:
a rotation unit which rotates the radiation detector around the patient; and
an image generation unit which generates a first image by using only radiation detection data acquired in a non-breathing state among the radiation detection data acquired by said radiation detector in a breathing state of the patient and the non-breathing state thereof with iterating an instruction of breathing and an instruction of non-breathing by breath holding alternately to the patient and a second image by using radiation detection data acquired in the non-breathing state and the breathing state,
wherein said radiation detector is configured to acquire data at both breathing periods and at non-breathing periods, the breathing and the non-breathing periods are associated to alternating radiographic directions, that are arranged at regular sectional intervals circularly around the patient, and the rotation unit is configured to stop the rotation of the radiation detector during the acquisition of data at the respective alternating radiographic directions.

14. A nuclear medical diagnostic equipment as defined in claim 13, further comprising an image-display-method setting unit which displays the first image and the second image on a display unit simultaneously.

15. A nuclear medical diagnostic equipment as defined in claim 13, wherein said image generation unit includes a data-ratio setting unit which sets a rate of the radiation detection data for use in the image generation, in the radiation detection data acquired in the breathing state, and it generates the image by using the radiation detection data at the rate set by said data-ratio setting unit.

16. A data acquisition method for a nuclear medical diagnosis wherein radiation which is emitted by a nuclide administered into a body of a patient is detected as projection data by a radiation detector, the radiation detector configured to be rotated around the patient, comprising the steps of:
instructing the patient on a period of breathing and on a period of non-breathing;
obtaining identification information which identifies a breathing state of the patient and a non-breathing state thereof based on breath holding;
acquiring projection data by said radiation detector at both the breathing periods and at the non-breathing periods, the breathing periods and the non-breathing periods are associated to alternating radiographic directions, that are arranged at regular sectional intervals circularly around the patient, and stopping the rotation of the radiation detector at the respective alternating radiographic directions during the stop of acquiring projection data;
storing the projection data in a manner to be capable of identifying whether the projection data have been acquired in the non-breathing state or in the breathing state, by using the identification information; and
generating a first image by using only projection data acquired in the non-breathing state and a second image by using projection data acquired in the non-breathing state and the breathing state.

17. A data acquisition method for a nuclear medical diagnosis wherein radiation which is emitted by a nuclide administered into a body of a patient is detected as projection data by a radiation detector, the radiation detector configured to be rotated around the patient, comprising the steps of:
acquiring projection data by said radiation detector at both breathing periods and at non-breathing periods, the breathing periods and the non-breathing periods are associated to alternating radiographic directions, that are arranged at regular sectional intervals circularly around the patient, and stopping the rotation of the radiation detector at the respective alternating radiographic directions during the stop of acquiring projection data;
storing the projection data which have been acquired with iterating an instruction of breathing and an instruction of non-breathing by breath holding alternately to the patient by the radiation detector in a breathing state of the patient and a non-breathing state thereof based on breath holding, respectively, in a manner to be capable of identifying whether the projection data have been acquired in the non-breathing state or in the breathing state; and
generating a first image by using only projection data acquired in the non-breathing state and a second image by using projection data acquired in the non-breathing state and the breathing state.

18. The nuclear medical diagnostic equipment according to claim 1, wherein the rotation unit is configured to move step-wise from a first radiographic direction to a second radiographic direction by moving by a constant angle of rotation, and the radiation detector is configured to detect radiation detection data in the state of breathing at the first radiographic direction, and to detect radiation detection data in the state of non-breathing in the second radiographic direction.

19. The data acquisition method according to claim 16, wherein said step of acquiring projection data further comprises:

moving the radiation detector step-wise from a first radiographic direction to a second radiographic direction by a constant angle of rotation;

detecting radiation detection data in the state of breathing at the first radiographic direction; and detecting radiation detection data in the state of non-breathing in the second radiographic direction.

\* \* \* \* \*